(12) United States Patent
Moshos et al.

(10) Patent No.: US 10,941,161 B2
(45) Date of Patent: Mar. 9, 2021

(54) INTERMEDIATES IN THE SYNTHESIS OF CEPHALOSPORIN COMPOUNDS

(71) Applicant: Merck Sharp & Dohme Corp., Rahway, NJ (US)

(72) Inventors: Kristos Adrian Moshos, Belmont, MA (US); Valdas Jurkauskas, Cambridge, MA (US); Giovanni Fogliato, Barzana (IT); Manuel Scanu, Milan (IT); You Seok Hwang, Windham, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 183 days.

(21) Appl. No.: 16/291,893

(22) Filed: Mar. 4, 2019

(65) Prior Publication Data
US 2019/0225624 A1    Jul. 25, 2019

Related U.S. Application Data

(63) Continuation of application No. 15/503,564, filed as application No. PCT/US2015/045240 on Aug. 14, 2015, now Pat. No. 10,221,196.

(60) Provisional application No. 62/037,722, filed on Aug. 15, 2014.

(51) Int. Cl.
    C07D 501/04     (2006.01)
    C07D 501/56     (2006.01)
    C07D 501/24     (2006.01)
    C07D 501/54     (2006.01)

(52) U.S. Cl.
    CPC ......... *C07D 501/56* (2013.01); *C07D 501/04* (2013.01); *C07D 501/24* (2013.01); *C07D 501/54* (2013.01); *C07B 2200/13* (2013.01); *Y02P 20/55* (2015.11)

(58) Field of Classification Search
    CPC .................................................... C07D 501/04
    See application file for complete search history.

(56) References Cited

U.S. PATENT DOCUMENTS

| 5,401,734 | A  | 3/1995  | Yamanaka et al. |
| 7,129,232 | B2 | 10/2006 | Ohki et al.     |
| 7,192,943 | B2 | 3/2007  | Yamanaka et al. |
| 9,695,196 | B2 | 7/2017  | Moshos et al.   |
| 10,221,196 | B2 | 3/2019 | Moshos et al.   |
| 2014/0274958 | A1 | 9/2014 | Lai et al.     |

FOREIGN PATENT DOCUMENTS

AU    2005202802 A1    6/2005

OTHER PUBLICATIONS

Ayoko Toda, et al., Synthesis and SAR of novel parenteral antipseudonmonal cephalosporins: Discovery of FR 264205, Bioorganic and Medicinal Chemistry Letters, 2008, pp. 4849-4852, vol. 18.
Kenji Murano, Structural Requirements for the stability of novel cephalosporins to AMPC B-lactamase based on 3D-structure, Bioorganic and Medicinal Chemistry, Nov. 22, 2007, 2261-2275, 16.
PCT Search Report for PCT/US2015/045240, dated Jan. 19, 2016, 3 pages.
U.S. Appl. No. 15/503,564, filed Aug. 14, 2015.

*Primary Examiner* — Emily A Bernhardt
*Assistant Examiner* — Laura M Daniel
(74) *Attorney, Agent, or Firm* — J. Eric Thies; John C. Todaro

(57) ABSTRACT

Described herein are crystalline forms of a compound of formula (III'), including toluene solvates of TATD-CLE, as well as processes for the preparation thereof and use thereof in the preparation of cephalosporin compounds such as ceftolozane.

20 Claims, 13 Drawing Sheets

FIG. 8

| Name of The Solvent | Reported level in TATD-CLE (Compound III) |
|---|---|
| Toluene | 11.70% |

INTERMEDIATES IN THE SYNTHESIS OF CEPHALOSPORIN COMPOUNDS

1. CROSS REFERENCE TO RELATED APPLICATIONS

This application is a Continuation of U.S. Ser. No. 15/503,564, filed Feb. 14, 2017, now U.S. Pat. No. 10,221,196, which is a U.S. National Phase application under 35 U.S.C. § 371 of PCT Application No. PCT/US2015/045240, filed Aug. 14, 2015, which claims priority under 35 U.S.C. § 119(e) from U.S. Ser. No. 62/037,722, filed Aug. 15, 2014, the contents of which are incorporated by reference in their entirety.

2. TECHNICAL FIELD

This disclosure relates to the solid forms of an intermediate used in manufacture of antibacterial cephalosporins such as ceftolozane.

3. BACKGROUND

Crystalline forms of compounds are often important when the compound is used in pharmaceutical applications. Compared with an amorphous solid, the solid physical properties of a crystalline compound can be markedly different, affecting its suitability for pharmaceutical use. For example, different forms of a crystalline compound, including polymorphs and solvates, can incorporate different types and/or different amounts of impurities. Different solid forms of a compound can also vary in chemical stability when exposed to different environmental stressors such as heat and/or water.

Ceftolozane is a cephalosporin antibacterial agent, also referred to as CXA-101, FR264205, or by chemical names such as (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of compound (VI) (FIG. 1A) that can be formulated for intravenous administration or infusion.

(VI)

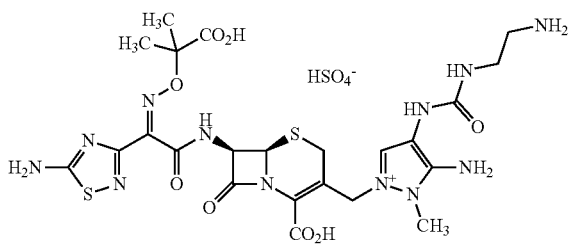

Ceftolozane can be obtained using methods described in U.S. Pat. Nos. 7,129,232 and 7,192,943, as well as Toda et al., "Synthesis and SAR of novel parenteral anti-pseudomonal cephalosporins: Discovery of FR264205," *Bioorganic & Medicinal Chemistry Letters*, 18, 4849-4852 (2008), each of which are incorporated herein by reference in their entirety. An important intermediate in the known syntheses of ceftolozane is compound (III) (also referred to herein as "TATD-CLE").

(III)

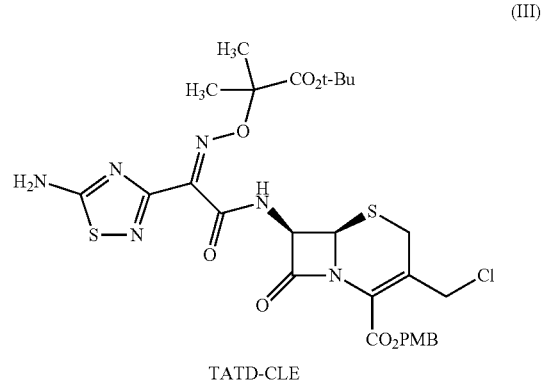

TATD-CLE

The published reaction to make compound (III) involves an isolation using solvents such as, for example, diisopropyl ether. However, this is not a preferred process because diisopropyl ether has significant vapor pressure at room temperature, is highly flammable and has the potential to form peroxides upon storage.

Given the multi-step synthesis of ceftolozane and its commercial importance, there is a need to develop new approaches for each of the individual reaction steps in the synthesis of ceftolozane, such as the synthesis of new forms of compound (III), to increase reaction yields, safety, and overall efficiency in the synthetic process.

4. SUMMARY

Provided herein is a crystalline form of a compound of formula (III'):

(III')

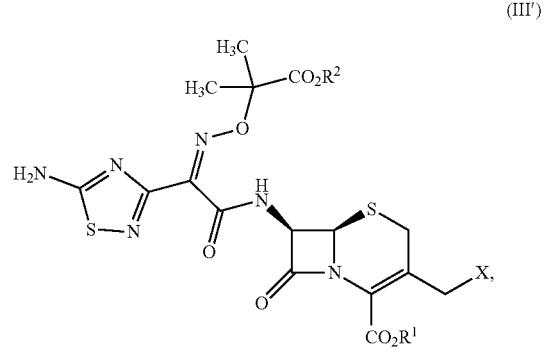

wherein X is Cl, Br, or I; and $R^1$ and $R^2$ are each independently an oxygen protecting group;

processes for making the crystalline form, and use of said form in the synthesis of antibacterial cephalosporins such as ceftolozane.

In some embodiments, $R^1$ and $R^2$ are each independently tert-butyldimethylsilyl, tert-butyl, 4-methoxybenzyl, 2-methoxybenzyl, or triphenylmethyl.

In some embodiments, the compound of formula (III') has the structure of compound (III):

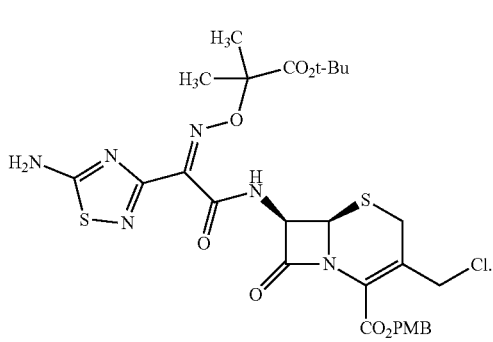
(III)

In some embodiments, the crystalline form is a solvate of an aromatic solvent. In some embodiments, the aromatic solvent is toluene, xylene, ethylbenzene, benzene, cumene, or mixtures thereof. In some preferred embodiments, the solvate is a toluene solvate. In some embodiments, the crystalline form has a 1:1 molar ratio of compound (III) to solvent.

In some embodiments, the crystalline form has an X-ray Powder Diffraction (XRPD) pattern comprising one or more characteristic peaks expressed in degrees 2θ at about 6.1, about 12.1, about 13.1, about 18.5, and about 24.3.

In some embodiments, the crystalline form has an X-ray Powder Diffraction (XRPD) pattern comprising one or more characteristic peaks expressed in degrees 2θ at about 7.3, about 10.0, about 11.6, about 17.7, and about 24.6.

In another aspect, provided herein is a process of preparing a crystalline form of a compound of formula (III'), comprising the step of admixing a non-crystalline form of a compound of formula (III') and an aromatic solvent to form an admixture comprising the crystalline form of a compound of formula (III'). In some embodiments, the process comprises cooling the admixture. In some embodiments, the process comprises the step of isolating the crystalline form of a compound of formula (III'), e.g., compound (III).

In another aspect, provided herein is a process of preparing a compound of formula (V"):

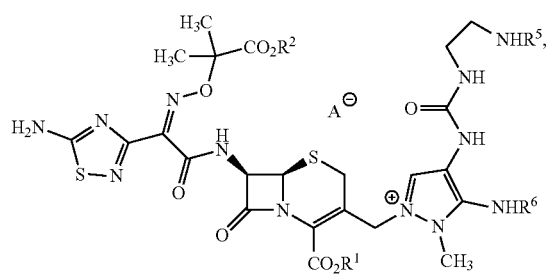
(V")

comprising admixing the crystalline form of a compound of formula (III') with a compound of formula (IV'):

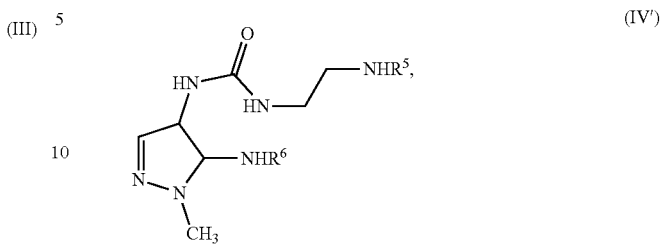
(IV')

wherein $R^1$ and $R^2$ are each independently an oxygen protecting group; $R^5$ and $R^6$ are each independently a nitrogen protecting group; and $A^\ominus$ is a pharmaceutically acceptable anion.

In some embodiments, $R^5$ and $R^6$ are each independently tert-butyl, tert-butoxycarbonyl, 2-trimethylsilylethoxycarbonyl, or triphenylmethyl.

In some embodiments, $A^\ominus$ is chloride, bromide, iodide, sulfate, bisulfate, toluenesulfonate, methanesulfonate, trifluoroacetate, or trifluoromethanesulfonate.

In some embodiments, the compound of formula (V") has the structure of compound (V):

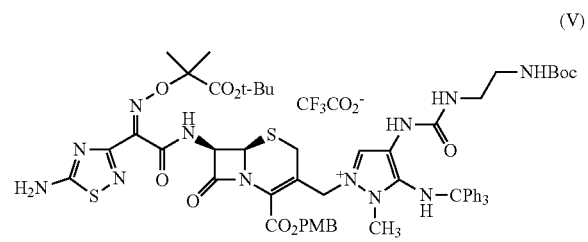
(V)

and the compound of formula (IV') has the structure of compound (IV):

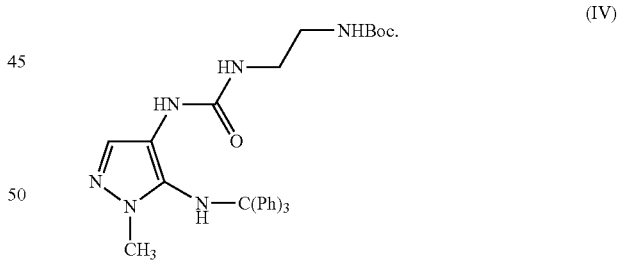
(IV)

In some embodiments, the process comprises the step of converting compound (V) to compound (VI):

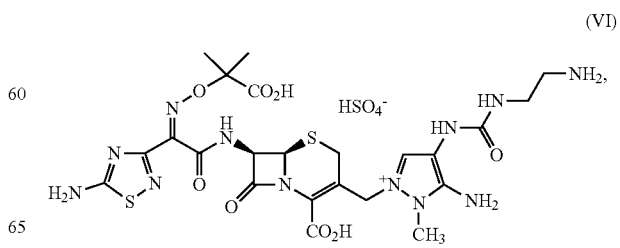
(VI)

comprising contacting compound (V) with trifluoroacetic acid.

In one aspect, provided herein is a toluene solvate of compound (III).

In one aspect, provided herein is a process for making a toluene solvate of compound (III) comprising the steps of admixing a non-crystalline form of compound (III) with an organic solvent comprising toluene to obtain the toluene solvate of compound (III).

In one aspect, provided herein is a process for making compound (V) comprising the step of admixing a toluene solvate of compound (III) with compound (IV).

5. BRIEF DESCRIPTION OF THE FIGURES

FIG. 1A is the chemical structure of ceftolozane sulfate.

FIG. 1B is an example synthetic scheme showing known methods of ceftolozane synthesis: see U.S. Pat. Nos. 7,129,232 and 7,192,943, as well as Toda et al., "Synthesis and SAR of novel parenteral anti-pseudomonal cephalosporins: Discovery of FR264205," Bioorganic & Medicinal Chemistry Letters, 18, 4849-4852 (2008).

FIG. 8 shows the residual solvent content in a toluene solvate of compound (III). The results showed the level of toluene present in TATD-CLE form 1.

6. DETAILED DESCRIPTION

6.1. Definitions

Figure 1A:
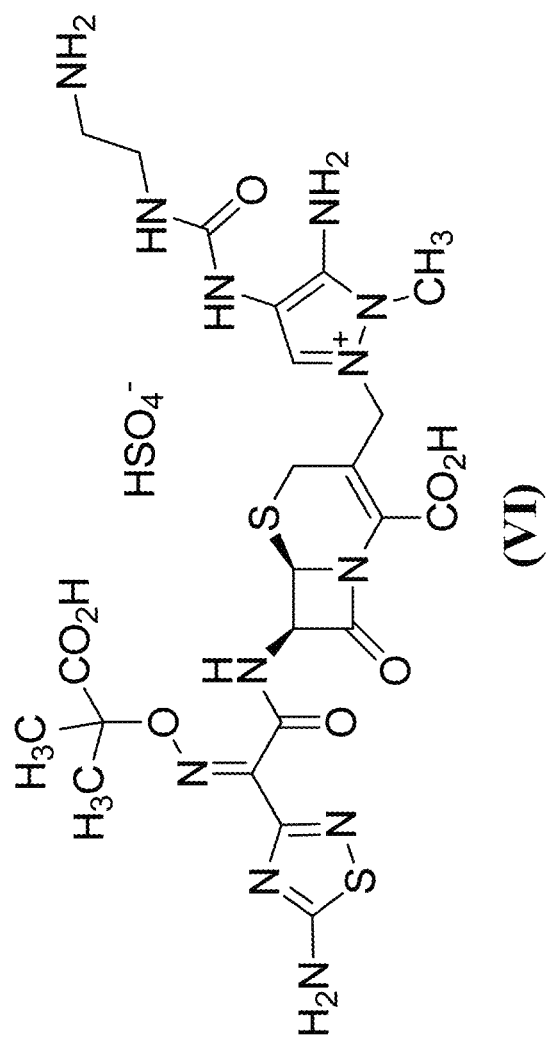
FIG. 1C is a synthetic scheme for preparing a ceftolozane starting material, a protected 5-amino-1-methylpyrazole, as disclosed in Toda et al.

As used herein, the following terms are intended to have the following meanings:

The term "substituted" refers to moieties having substituents replacing a hydrogen on one or more atoms on the indicated moiety. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "$C_{x-y}$ alkyl" refers to unsubstituted saturated hydrocarbon groups, including straight-chain alkyl and branched-chain alkyl groups that contain from x to y carbons in the chain. For example, $C_{1-6}$ alkyl is an alkyl group having one to six carbons.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "urea" as used herein includes a moiety that can be represented by the general formula:

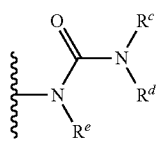

wherein $R^c$, $R^d$, and $R^e$ each independently represent a hydrogen, an alkyl, an alkenyl, —$(CH_2)_m$—$R^f$, or $R^c$ and $R^d$ taken together with the N atom to which they are attached complete a heterocycle having from 4 to 8 atoms in the ring structure; $R^f$ represents an aryl, a cycloalkyl, a cycloalkenyl, a heterocyclyl or a polycyclyl; and m is zero or an integer from 1 to 8. In preferred embodiments, only one of $R^c$ and $R^d$ is a carbonyl, e.g., $R^c$, $R^d$, and the nitrogen together do not form an imide. In even more preferred embodiments, $R^c$ and $R^d$ (and optionally $R^e$) each independently represent a hydrogen, an alkyl, an alkenyl, or —$(CH_2)_m$—$R^f$.

As used herein, a "protecting group" is a moiety that masks the chemical reactivity of a functional group during one or more reactions. In an illustrative example, an oxygen protecting group such as 4-methoxybenzyl (PMB) can be introduced at one step to mask the chemical reactivity of an —OH function on a carboxylic acid or an alcohol during one or more reactions then removed under acidic conditions to allow the —OH group to undergo reaction in the next step. A protecting group can be any one known in the art, such as those described in Wuts, P. G. M.; Greene, T. W. *Greene's Protective Groups in Organic Synthesis*, 4$^{th}$ ed; John Wiley & Sons: Hoboken, N.J., 2007.

In some embodiments, the oxygen protecting group is a base-labile oxygen protecting group (i.e., one that is removed under basic conditions), such as a methyl group when used as an ester to protect a carboxylic acid (i.e., —COOH). In some embodiments, the oxygen protecting group is an acid-labile oxygen protecting group (i.e., one that is removed under acidic conditions), such as tert-butyldimethylsilyl (i.e., TBDMS), tert-butyl, 4-methoxybenzyl (i.e., PMB, MPM), 2-methoxybenzyl, or triphenylmethyl (i.e., trityl or Tr). In some embodiments, the oxygen protecting group is an oxidation-reduction sensitive oxygen protecting group, such as a benzyl ether which is removed under oxidative or reductive conditions, e.g., catalytic hydrogenation conditions.

In some embodiments, the nitrogen protecting group is a base-labile nitrogen protecting group (i.e., one that is removed under basic conditions), such as 9-fluorenylmethyl carbamate (Fmoc). In some embodiments, the nitrogen protecting group is an acid-labile nitrogen protecting group (i.e., one that is removed under acid conditions), such as tert-butyl, tert-butoxycarbonyl (i.e., tert-butyloxycarbonyl, Boc, or BOC), 2-trimethylsilylethoxycarbonyl (i.e., Teoc), or triphenylmethyl. In some embodiments, the nitrogen protecting group is an oxidation-reduction sensitive nitrogen protecting group, such as a benzyl or benzyloxycarbonyl, which can be removed under oxidative or reductive conditions, e.g., under catalytic hydrogenation conditions.

Pharmaceutically acceptable salts are known to those of skill in the art. Pharmaceutically acceptable salts can be prepared in situ during the final isolation and purification of the compound, or by separately contacting a purified compound with a suitable organic or inorganic acid, and isolating the salt thus formed. Representative salts include the hydrobromide, hydrochloride, hydrogen iodide, sulfate, bisulfate, phosphate, nitrate, acetate, valerate, oleate, palmitate, stearate, laurate, benzoate, lactate, tosylate, citrate, maleate, fumarate, succinate, tartrate, naphthylate, mesylate, edisylate, glucoheptonate, lactobionate, laurylsulfonate salts, and amino acid salts, and the like. See, for example, Berge et al. 1977, "Pharmaceutical Salts," J. Pharm. Sci. 66: 1-19.

6.2. Crystalline Forms of a Compound of Formula (III')

Provided herein are crystalline forms of a compound of formula (III'), processes of making crystalline forms of a compound of formula (III'), and use of said forms in the synthesis of antibacterial cephalosporins (e.g., ceftolozane).

Disclosed herein is a crystalline form of a compound of formula (III'):

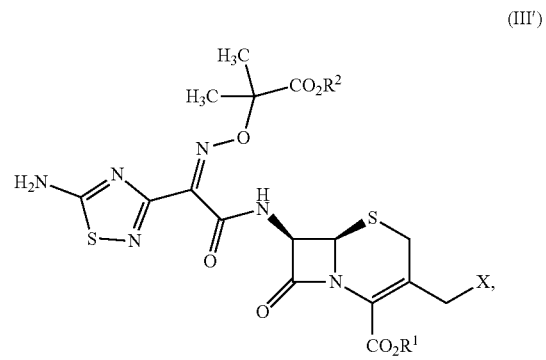

(III')

wherein
X is Cl, Br, or I; and
$R^1$ and $R^2$ are each independently an oxygen protecting group.

In some embodiments, X is Cl.

In some embodiments, $R^1$ is an acid-labile oxygen protecting group. In some embodiments, $R^1$ is selected from the group consisting of: tert-butyldimethylsilyl, tert-butyl, 4-methoxybenzyl, 2-methoxybenzyl, or triphenylmethyl. In some embodiments, $R^1$ is 4-methoxybenzyl.

In some embodiments, $R^2$ is an acid-labile oxygen protecting group. In some embodiments, $R^2$ is selected from the group consisting of: tert-butyldimethylsilyl, tert-butyl, 4-methoxybenzyl, 2-methoxybenzyl, or triphenylmethyl. In some embodiments, $R^2$ is tert-butyl.

In some embodiments, $R^1$ and $R^2$ are each independently an acid-labile oxygen protecting group. In some embodiments, $R^1$ and $R^2$ are each independently tert-butyldimethylsilyl, tert-butyl, 4-methoxybenzyl, 2-methoxybenzyl, or triphenylmethyl. In some embodiments, $R^1$ is 4-methoxybenzyl, and $R^2$ is tert-butyl.

In some embodiments, the crystalline form of a compound of formula (III') is a solvate. In some embodiments, the crystalline form is a solvate of an aromatic solvent. In some embodiments, the crystalline form is a solvate of toluene, xylene, ethylbenzene, benzene, or cumene, or mixtures thereof, preferably toluene. When crystalline forms are solvated, they can exist in varying molar ratios of compound to solvent within the unit cell. In some embodiments, the molar ratio of a compound of formula (III') to solvent is in a range of from about 1:3 to about 4:1, such as about 1:2 to 3:1, about 1:2 to 2:1, about 1:2 to 1:1, about 1:1 to 3:1, or about 1:1 to 2:1. In some embodiments, the molar ratio of a compound of formula (III') to solvent is about 1:3, about 1:2, about 1:1, about 1.5:1, about 2:1, about 2.5:1, about 3:1, or about 4:1. In a preferred embodiment, the molar ratio of a compound of formula (III') to solvent is about 1:1.

In some embodiments, the crystalline form is not solvated. In some embodiments, the crystalline form is substantially free of solvent.

In some embodiments, the crystalline form of a compound of formula (III') has the structure of a compound of formula (III) ("compound (III)"):

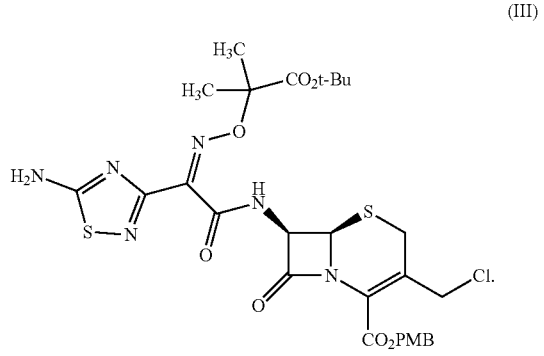

(III)

Figure 3A:
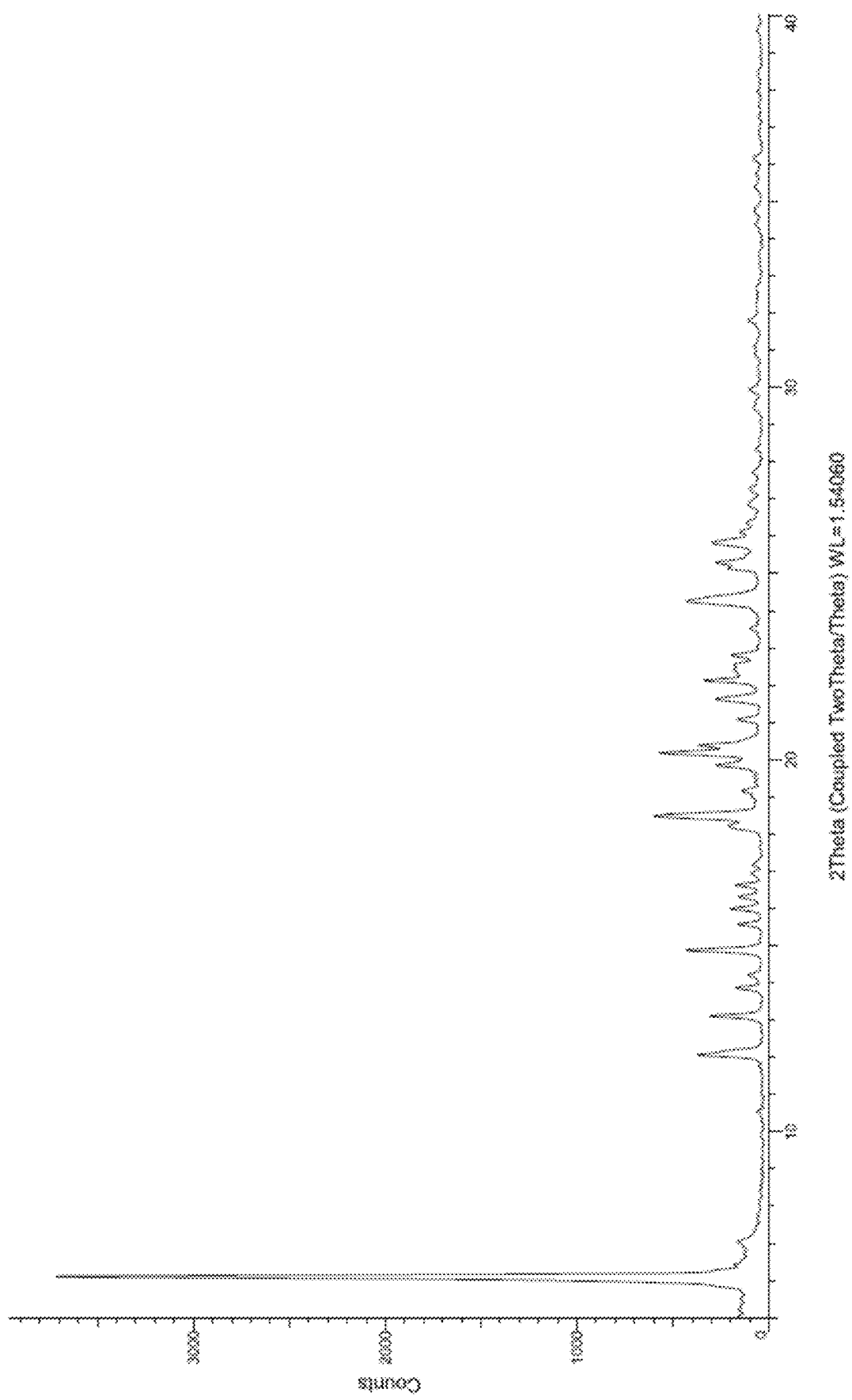
FIG. 3A depicts a representative X-ray powder diffraction pattern of a crystalline toluene solvate of compound (III). The crystalline toluene solvate characterized by the XRPD found in this figure is referred to herein as "compound (III) form 1" or "TATD-CLE form 1".

In some embodiments, the crystalline form of a compound of formula (III'), e.g., compound (III), has an X-ray powder diffraction pattern comprising one or more, two or more, three or more, four or more, or five or more characteristic peaks expressed in degrees 2θ at 6.1±0.2, 12.1±0.2, 13.1±0.2, 18.5±0.2, and 24.3±0.2. In some embodiments, the crystalline form has an XRPD pattern comprising the peaks as shown in Table 1. In some embodiments, the X-ray powder diffraction pattern is substantially as shown in FIG. 3A.

Figure 3B:
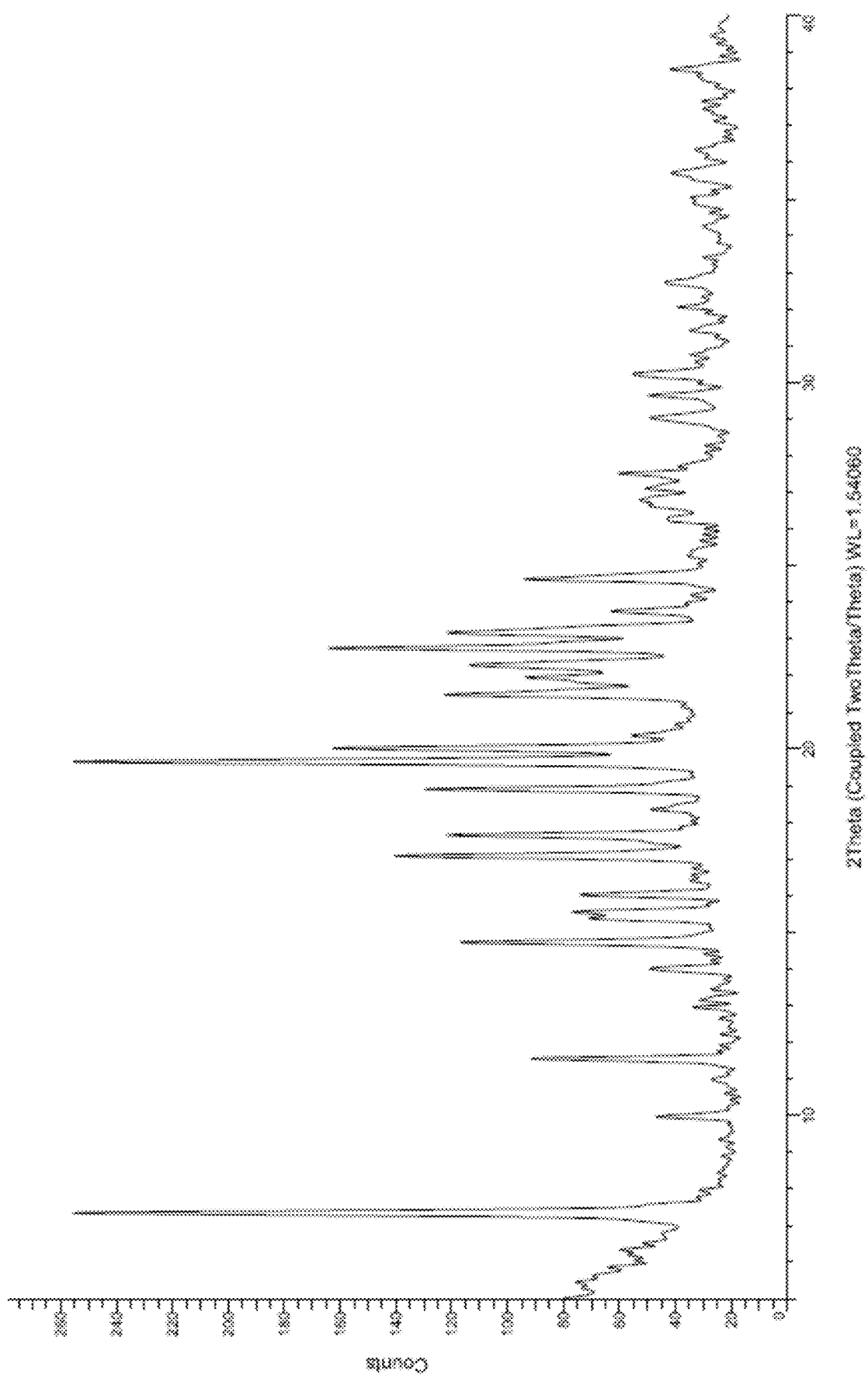
FIG. 3B depicts a representative X-ray powder diffraction pattern of a crystalline form of compound (III). The crystalline form characterized by the XRPD found in this figure is referred to herein as "compound (III) form 2" or "TATD-CLE form 2".

In some embodiments, the crystalline form of a compound of formula (III'), e.g., compound (III), has an X-ray powder diffraction pattern comprising one or more, two or more, three or more, four or more, or five or more characteristic peaks expressed in degrees 2θ at 7.3±0.2, 10.0±0.2, 11.6±0.2, 17.7±0.2, and 24.6±0.2. In some embodiments, the crystalline form has an XRPD pattern comprising the peaks as shown in Table 2A. In some embodiments, the X-ray powder diffraction pattern is substantially as shown in FIG. 3B.

In some embodiments, the crystalline form of a compound of formula (III'), e.g., compound (III), has an X-ray powder diffraction pattern comprising one or more, two or more, three or more, four or more, or five or more characteristic peaks expressed in degrees 2θ at 7.1±0.2, 12.4±0.2, 18.5±0.2, 19.3±0.2, and 25.5±0.2. In some embodiments, the crystalline form has an XRPD pattern comprising the peaks as shown in Table 2B. In some embodiments, the X-ray powder diffraction pattern is substantially as shown in FIG. 3D.

Figure 4:
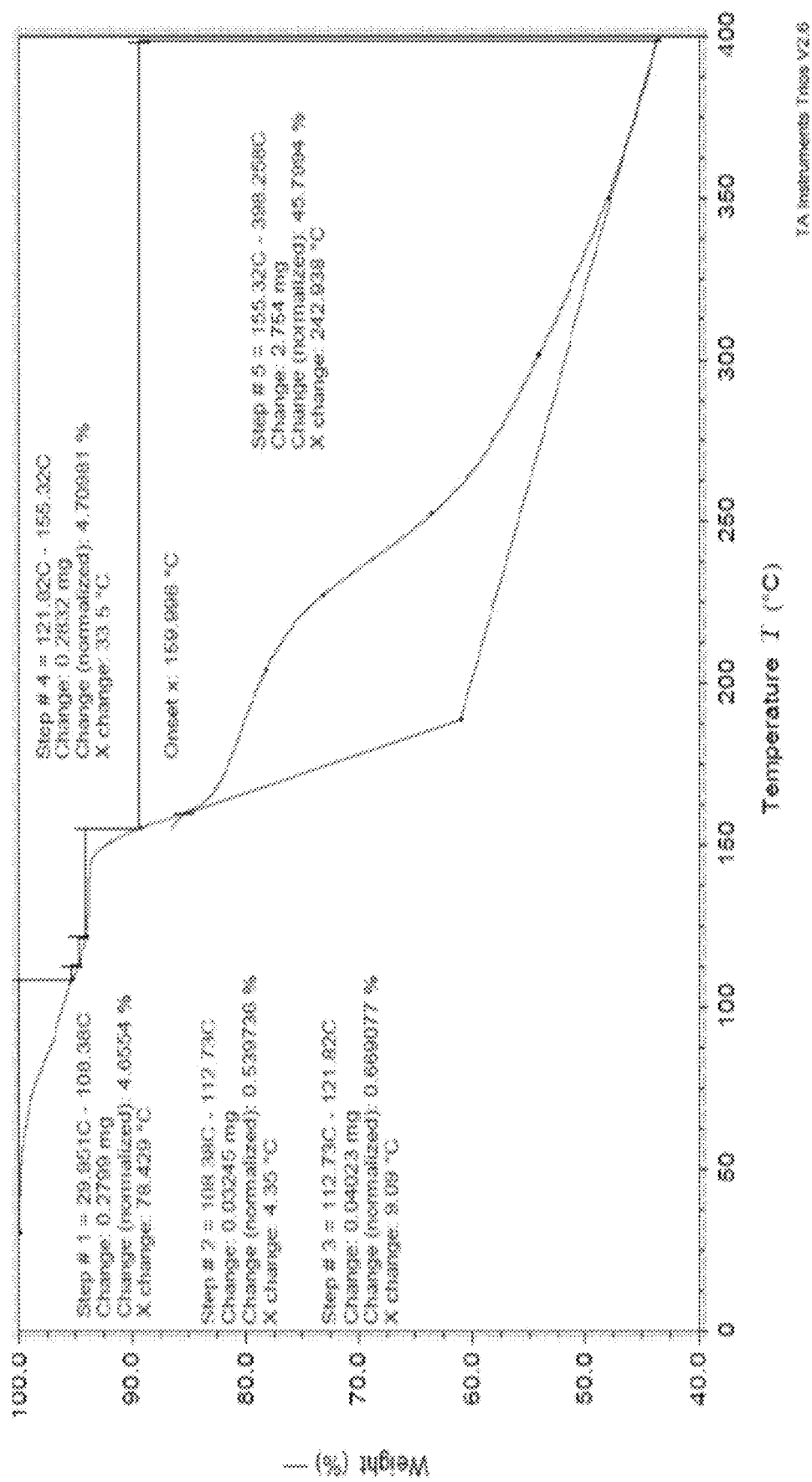
FIG. 4 is a thermogravimetric analysis (TGA) curve for compound (III) form 1.

In some embodiments, the crystalline form of a compound of formula (III'), e.g., compound (III), has a thermogravimetric analysis thermogram substantially as shown in FIG. 4.

Figure 5:
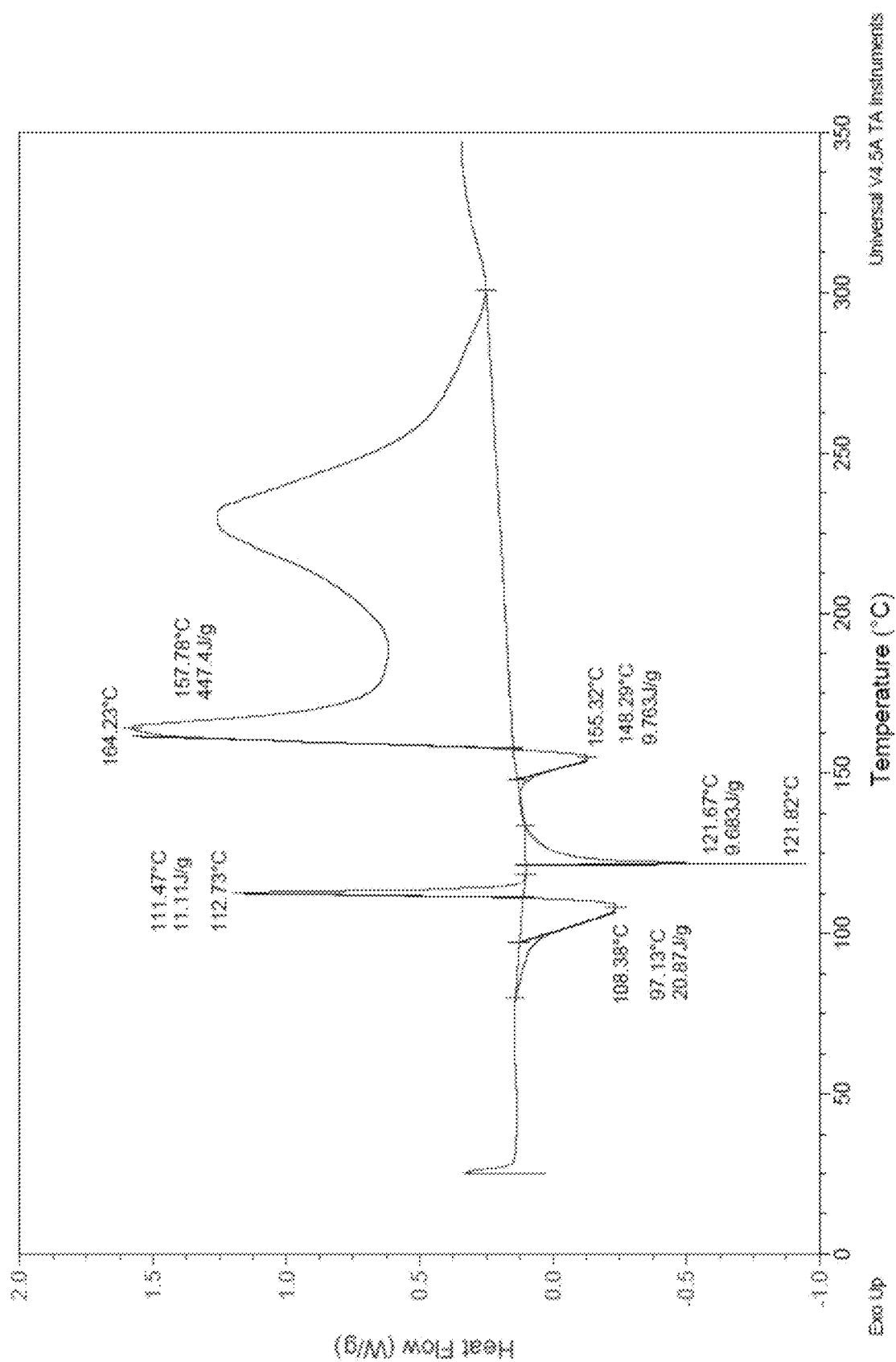
FIG. 5 is a differential scanning calorimetry (DSC) thermogram for compound (III) form 1.

In some embodiments, the crystalline form of a compound of formula (III'), e.g., compound (III), has a differential scanning calorimetry thermogram substantially as shown in FIG. 5.

6.3. Crystalline Forms of TATD-CLE

Provided herein are crystalline forms of compound (III), e.g., a toluene solvate of compound (III) ("TATD-CLE toluene solvate"), processes of making crystalline forms (such as toluene solvates) of compound (III), and use of said forms in the synthesis of antibacterial cephalosporins such as ceftolozane. The toluene solvates of TATD-CLE are advantageous in that they can be obtained in crystalline form, making them particularly suitable for use in the manufacture of pharmaceutically important cephalosporins, such as ceftolozane and salts of ceftolozane (e.g., compounds (Vb) or (VI)).

Provided herein is a toluene solvate of compound (III):

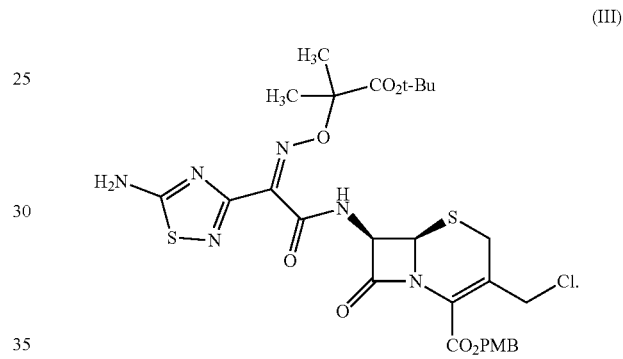

(III)

The toluene solvate of compound (III) ("TATD-CLE") can be crystalline.

As illustrated in FIG. 3A and FIG. 3B, at least two crystalline forms have been characterized by X-Ray Powder Diffraction (XRPD), e.g, TATD-CLE form 1 (FIG. 3A) and TATD-CLE form 2 (FIG. 3B). TATD-CLE form 1 can be converted to yet another TATD-CLE form 2 by heating to about 108° C. TATD-CLE form 2 was formed by heating in a differential scanning calorimeter. This sample was taken from the calorimeter and subsequently analyzed by XRPD to indicate the formation of crystalline TATD-CLE form 2.

Figure 3C:
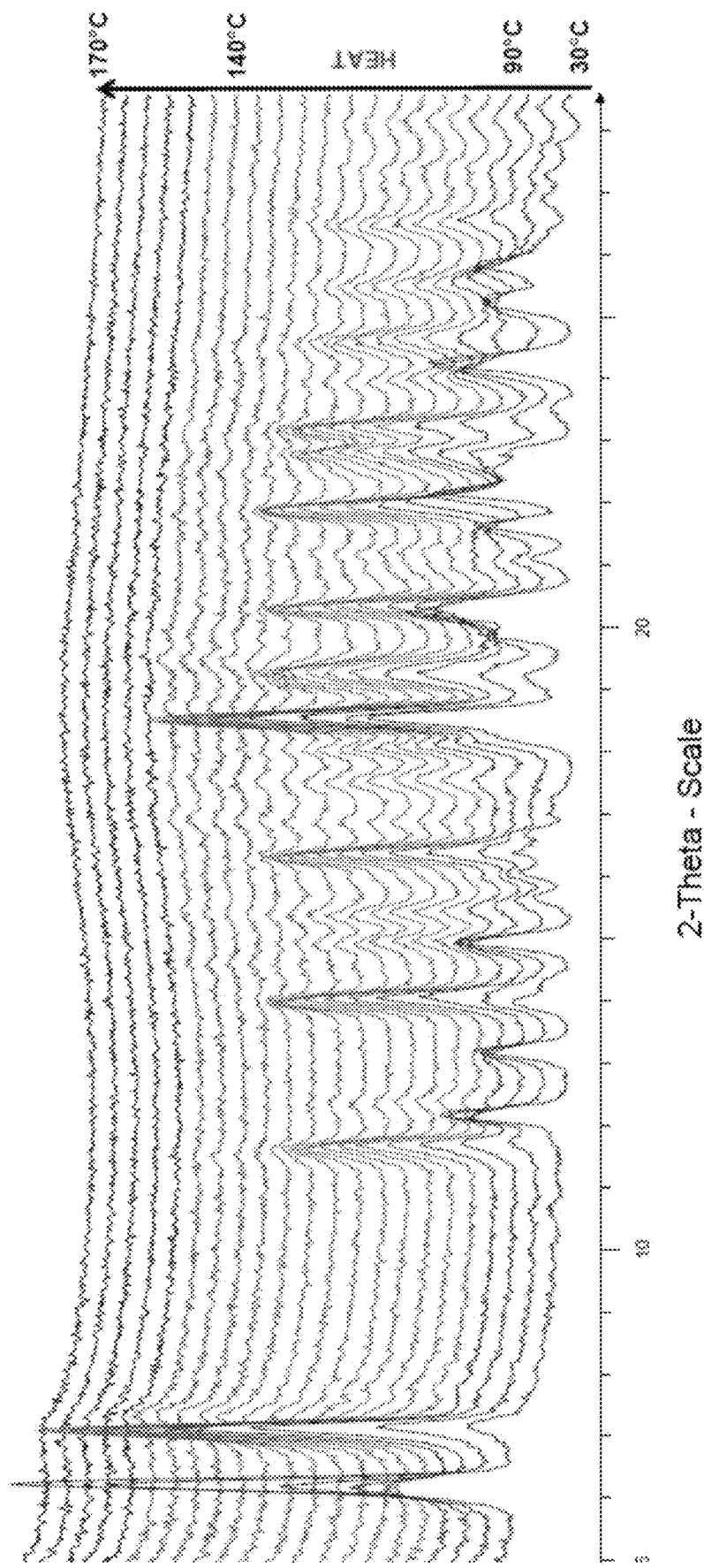
FIG. 3C depicts variable temperature X-ray powder diffraction patterns (VT-XRPD) of the crystalline form of compound (III). The initial spectrum is of TATD-CLE form 1.
Figure 3D:
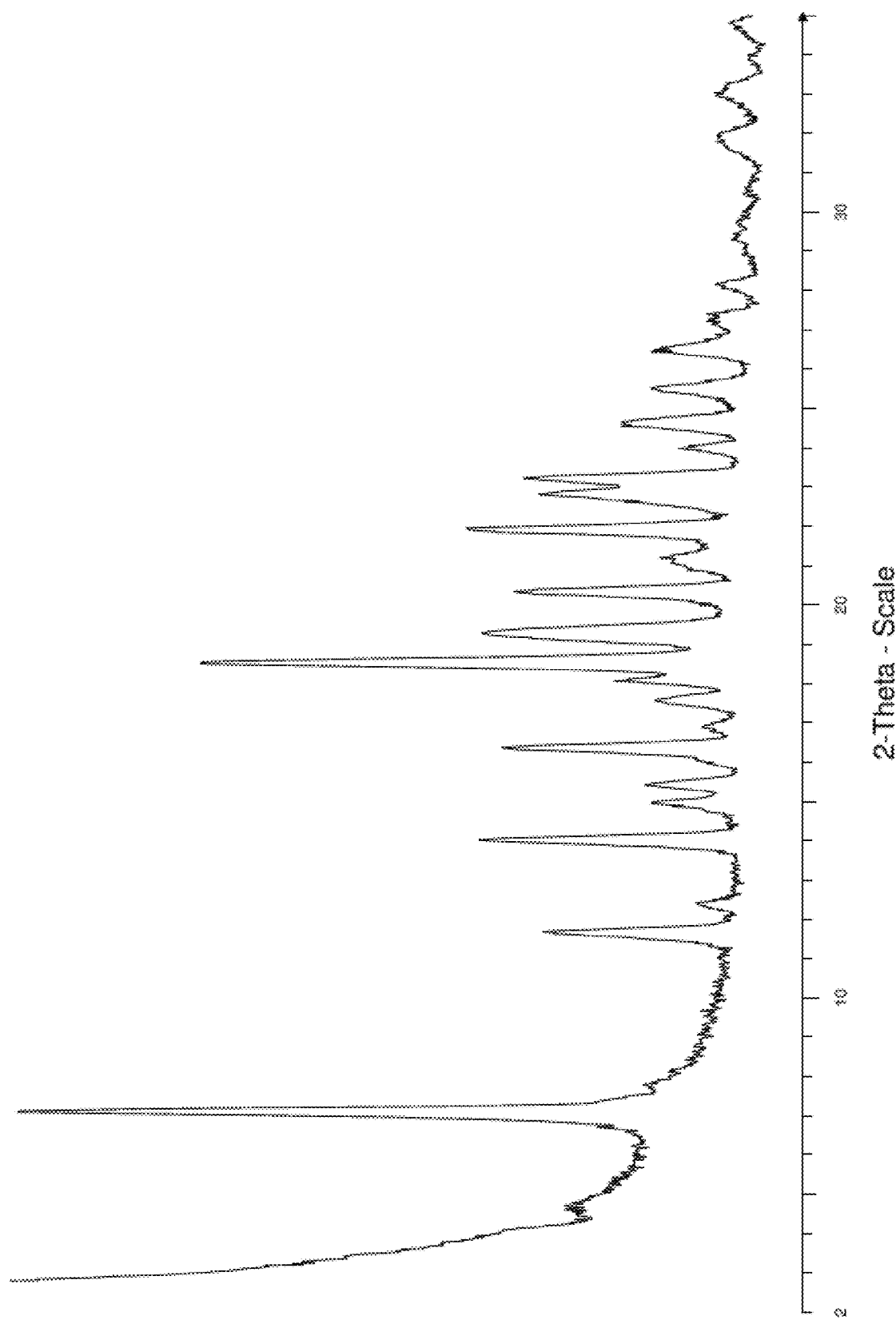
FIG. 3D depicts an exemplary variable temperature X-ray powder diffraction pattern of the crystalline form of compound (III) at 110° C. obtained from heating a sample of TATD-CLE form 1.

Additionally, another crystalline form of a compound of formula (III'), TATD-CLE form 3, is formed upon heating as shown in the VT-XRPD in FIG. 3C. As shown in FIG. 3D, TATD-CLE form 3 is produced from TATD-CLE form 1 upon heating to 110° C. in the X-ray powder diffractometer.

In one embodiment, TATD-CLE form 1 can be identified by an XRPD pattern comprising one or more, two or more, three or more, four or more, or five or more characteristic peaks expressed in degrees 2θ at about 6.1, about 12.1, about 13.1, about 18.5, and about 24.3. In another embodiment, TATD-CLE form 1 can be identified by an XRPD pattern comprising one or more, two or more, three or more, four or more, or five or more characteristic peaks expressed in degrees 2θ at 6.1±0.2, 12.1±0.2, 13.1±0.2, 18.5±0.2, and 24.3±0.2. In some embodiments, the crystalline TATD-CLE form 1 has an XRPD pattern comprising the peaks as shown in Table 1. In some embodiments, the crystalline TATD-CLE form 1 has an XRPD pattern substantially as shown in FIG. 3A.

TATD-CLE form 2 can be identified by an XRPD pattern comprising one or more, two or more, three or more, four or more, or five or more characteristic peaks expressed in degrees 2θ at about 7.3, about 10.0, about 11.6, about 17.7, and about 24.6. In another embodiment, TATD-CLE form 2 can be identified by an XRPD pattern comprising one or more, two or more, three or more, four or more, or five or more characteristic peaks expressed in degrees 2θ at 7.3±0.2, 10.0±0.2, 11.6±0.2, 17.7±0.2, and 24.6±0.2. In some embodiments, the crystalline TATD-CLE form 2 has an XRPD pattern comprising the peaks as shown in Table 2A. In some embodiments, the crystalline TATD-CLE form 2 has an XRPD pattern substantially as shown in FIG. 3B.

TATD-CLE form 3 can be identified by an XRPD pattern comprising one or more, two or more, three or more, four or more, or five or more characteristic peaks expressed in degrees 2θ at about 7.1, about 12.4, about 18.5, about 19.3, and about 25.5. In another embodiment, TATD-CLE form 3 can be identified by an XRPD pattern comprising one or more, two or more, three or more, four or more, or five or more characteristic peaks expressed in degrees 2θ at 7.1±0.2, 12.4±0.2, 18.5±0.2, 19.3±0.2, and 25.5±0.2. In some embodiments, the crystalline TATD-CLE form 3 has an XRPD pattern comprising the peaks as shown in Table 2B. In some embodiments, the crystalline TATD-CLE form 3 has an XRPD pattern substantially as shown in FIG. 3D.

In an embodiment, the toluene solvate of compound (III), i.e., TATD-CLE form 1, is characterized by an XRPD pattern having one or more, two or more, three or more, four or more, or five or more peaks at substantially the angles (2θ±0.2) of Table 1. In another embodiment, TATD-CLE form 1 is characterized by an X-ray powder diffraction pattern that is substantially the same as the spectra of FIG. 3A.

In an embodiment, the crystalline form of compound (III), i.e., TATD-CLE form 2, is characterized by an X-ray powder diffraction pattern having one or more, two or more, three or more, four or more, or five peaks at substantially the angles (2θ±0.2) of Table 2A. In another embodiment, TATD-CLE form 2 is characterized by an X-ray powder diffraction pattern that is substantially the same as the spectra of FIG. 3B.

In an embodiment, the crystalline form of compound (III), i.e., TATD-CLE form 3, is characterized by an X-ray powder diffraction pattern having one or more, two or more, three or more, four or more, or five peaks at substantially the angles (2θ±0.2) of Table 2B. In another embodiment, TATD-CLE form 3 is characterized by an X-ray powder diffraction pattern that is substantially the same as the spectra of FIG. 3D.

In another aspect, provided herein is a composition comprising a crystalline form of a compound of formula (III'), e.g., TATD-CLE toluene solvate. In an embodiment, the composition comprises TATD-CLE in one or more solid forms (e.g., TATD-CLE form 1 and/or TATD-CLE form 2 and/or TATD-CLE form 3). In a further embodiment, the composition comprises a compound of formula (III'), e.g., compound (III), having an XRPD pattern comprising one or more characteristic peaks expressed in degrees 2θ at about 6.1, about 12.1, about 13.1, about 18.5, and about 24.3 and/or a compound having an XRPD pattern comprising one or more characteristic peaks expressed in degrees 2θ at about 7.3, about 10.0, about 11.6, about 17.7, and about 24.6 and/or a compound having an XRPD pattern comprising one or more characteristic peaks expressed in degrees 2θ at about 7.1, about 12.4, about 18.5, about 19.3, and about 25.5. In addition, compositions comprising a compound of formula (III'), e.g., compound (III), e.g., TATD-CLE form 1 and/or TATD-CLE form 2 and/or TATD-CLE form 3, can be identified by XRPD patterns with diffractions at 2θ indicated in Table 1 (TATD-CLE form 1), in Table 2A (TATD-CLE form 2), and in Table 2B.

In another aspect, provided herein are compositions of crystalline compound of a compound of formula (III'), e.g., compound (III), characterized by an X-ray powder diffraction pattern having peaks at substantially the same angles (2θ) as the spectra of FIG. 3C (i.e., a mixture of TATD-CLE form 1 and TATD-CLE form 3).

TABLE 1

X-ray Powder Diffraction Peaks for TATD-CLE form 1

| Angle 2-Theta ° | Relative Intensity % |
|---|---|
| 6.105 | 99.7% |
| 7.036 | 2.2% |
| 12.076 | 9.1% |
| 13.111 | 7.4% |
| 13.866 | 3.6% |
| 14.210 | 1.7% |
| 14.881 | 10.7% |
| 15.577 | 3.1% |
| 15.995 | 4.1% |
| 16.319 | 2.9% |
| 16.627 | 3.4% |
| 16.942 | 1.3% |
| 17.182 | 1.1% |
| 18.221 | 4.3% |
| 18.490 | 15.0% |
| 19.160 | 2.1% |
| 19.856 | 5.8% |
| 20.183 | 13.9% |
| 20.377 | 8.3% |
| 21.080 | 2.8% |
| 21.631 | 5.9% |
| 22.134 | 7.6% |
| 22.529 | 3.3% |
| 22.804 | 3.8% |
| 23.533 | 1.2% |
| 24.268 | 10.2% |
| 25.147 | 4.1% |
| 25.297 | 5.8% |
| 25.832 | 6.3% |
| 26.124 | 2.3% |
| 26.370 | 1.3% |
| 26.874 | 1.3% |
| 27.283 | 1.2% |
| 27.733 | 1.1% |
| 29.946 | 1.5% |
| 31.809 | 1.5% |
| 36.153 | 1.1% |

TABLE 2A

X-ray Powder Diffraction Peaks for TATD-CLE form 2

| Angle 2-Theta ° | Relative Intensity % |
|---|---|
| 7.345 | 99.7% |
| 9.977 | 11.8% |
| 11.000 | 2.9% |
| 11.550 | 32.5% |
| 12.954 | 5.9% |
| 13.167 | 4.5% |
| 13.447 | 2.8% |
| 14.005 | 11.5% |
| 14.728 | 41.4% |
| 15.386 | 20.0% |
| 15.544 | 22.2% |
| 16.028 | 20.7% |
| 17.083 | 49.0% |
| 17.651 | 39.9% |
| 18.358 | 6.0% |

TABLE 2A-continued

X-ray Powder Diffraction Peaks for TATD-CLE form 2

| Angle 2-Theta ° | Relative Intensity % |
| --- | --- |
| 18.904 | 42.9% |
| 19.656 | 99.9% |
| 20.019 | 57.3% |
| 20.368 | 8.3% |
| 21.490 | 38.9% |
| 21.822 | 17.4% |
| 21.951 | 25.7% |
| 22.290 | 35.0% |
| 22.757 | 58.6% |
| 23.178 | 39.8% |
| 23.760 | 14.0% |
| 24.643 | 29.4% |
| 26.275 | 6.7% |
| 26.631 | 9.7% |
| 26.794 | 11.2% |
| 27.122 | 10.1% |
| 27.513 | 14.8% |
| 29.034 | 10.9% |
| 29.647 | 10.9% |
| 29.963 | 2.8% |
| 30.222 | 13.4% |
| 30.545 | 3.4% |
| 30.760 | 4.5% |
| 31.414 | 4.7% |
| 31.065 | 6.4% |
| 32.726 | 8.5% |
| 33.411 | 2.9% |
| 34.262 | 2.9% |
| 34.880 | 4.5% |
| 35.041 | 5.1% |
| 35.712 | 8.3% |
| 36.123 | 3.1% |
| 36.358 | 4.8% |
| 37.142 | 2.4% |

TABLE 2B

X-ray Powder Diffraction Peaks for TATD-CLE form 3

| Angle 2-Theta ° | Relative Intensity % |
| --- | --- |
| 7.084 | 100.0% |
| 11.672 | 33.0% |
| 12.396 | 13.7% |
| 14.020 | 41.1% |
| 14.938 | 19.4% |
| 15.397 | 20.2% |
| 16.051 | 14.0% |
| 16.333 | 38.3% |
| 16.881 | 13.0% |
| 17.552 | 18.8% |
| 18.064 | 24.2% |
| 18.523 | 76.6% |
| 19.264 | 40.8% |
| 20.359 | 36.9% |
| 20.889 | 14.8% |
| 21.065 | 16.7% |
| 21.189 | 18.5% |
| 21.931 | 42.8% |
| 22.813 | 33.5% |
| 23.220 | 35.7% |
| 23.997 | 16.0% |
| 24.632 | 23.1% |
| 25.515 | 19.3% |
| 27.246 | 12.3% |
| 28.164 | 11.4% |
| 29.311 | 9.5% |
| 31.819 | 11.4% |
| 32.967 | 11.4% |

FIG. 4 (TGA) and FIG. 5 (DSC) show TATD-CLE form 1 can be transformed by heating to around 108° C. A sample taken from the differential scanning calorimeter and analyzed by XRPD showed TATD-CLE form 2. Melting of TATD-CLE form 1 was observed at about 108° C., followed by recrystallization at about 111° C. Melting of the second crystalline form was observed at about 122° C., followed by degradation at about 150° C. Data from TGA are consistent with data observed from DSC.

FIG. 3C (VT-XRPD) shows formation of TATD-CLE form 3 from TATD-CLE form 1 upon heating. FIG. 3D shows the XRPD of crystalline TATD-CLE form 3 at 110° C. Table 2B describes the characteristic peaks of the crystal form at 110° C. present in the VT-XRPD.

Figure 7:
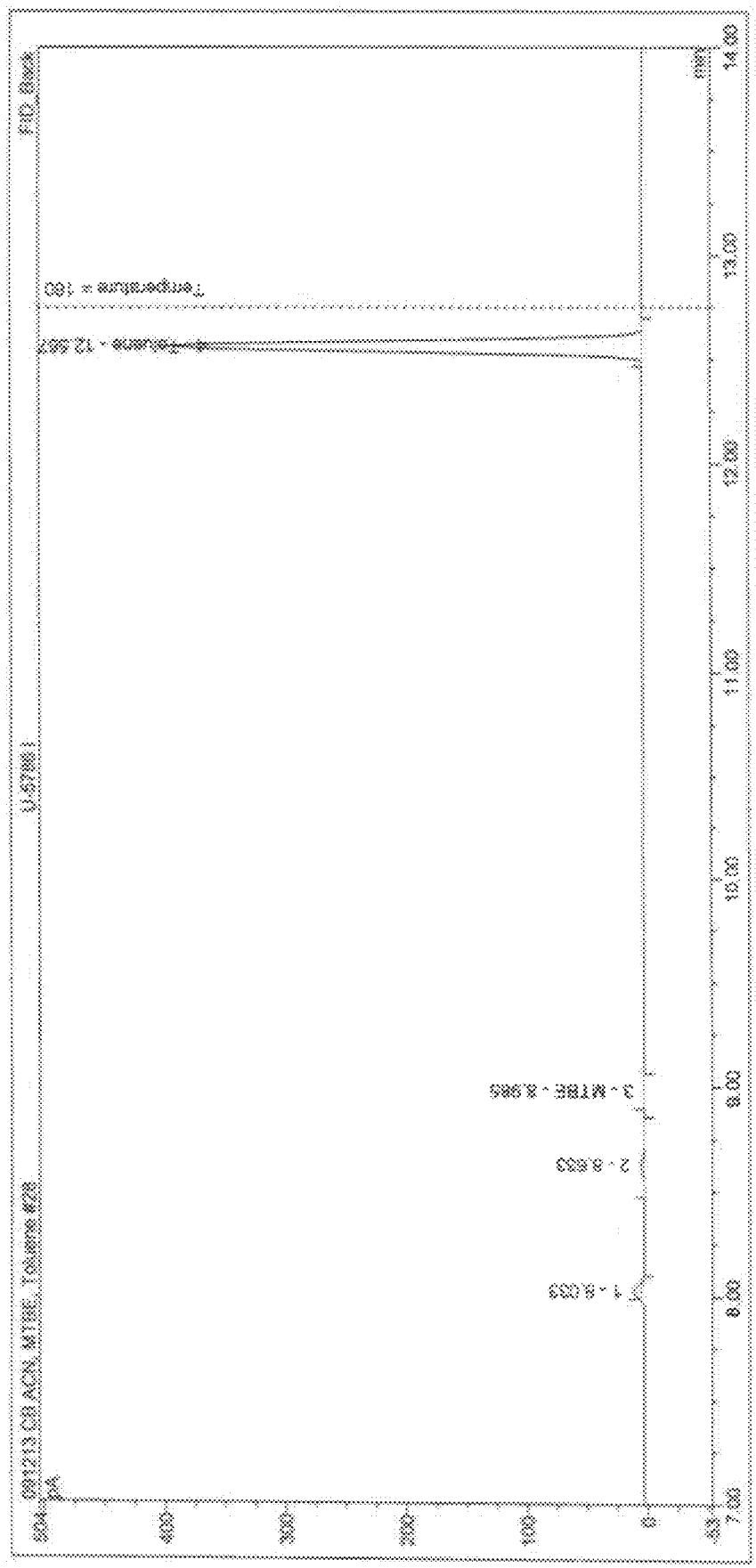
FIG. 7 shows the GC Chromatogram to analyze the toluene content of a toluene solvate of compound (III). The results showed the level of toluene present in TATD-CLE form 1.

The level of solvent, e.g., toluene, in a crystalline form of a compound of formula (III'), e.g., TATD-CLE toluene solvate (e.g., TATD-CLE form 1), can be determined by residual solvent content analysis by gas chromatography (e.g., FIG. 7). In an embodiment, a TATD-CLE toluene solvate contains between about 10% and about 15% toluene. In a further embodiment, a TATD-CLE toluene solvate contains about 11.70% of toluene.

6.4. Processes of Making a Crystalline Compound of Formula (III')

Disclosed herein is a process of making a crystalline compound of formula (III'), e.g., compound (III). Crystallization methods include methods to form a solid in a slow and controlled fashion to allow for ordered formation of a crystal lattice. Such methods include supersaturation of a solution comprising a compound to be crystallized. A number of methods known in the art can be applied to make a crystalline compound of formula (III'), including slow evaporation, slow cooling, vapor diffusion, and solvent diffusion.

In some embodiments, the process comprises the step of admixing a non-crystalline form of a compound of formula (III'), e.g., a non-crystalline form of compound (III), and an organic solvent to form an admixture, which comprises the crystalline form of a compound of formula (III'). In some cases, aging of the admixture affords a greater amount of the crystalline form.

A non-crystalline form of a compound as described herein, e.g., a compound of formula (III'), e.g., compound (III), can be in any non-crystalline state. Non-limiting embodiments of non-crystalline forms include solutions, e.g., in a non-aromatic organic solvent such as ethyl acetate or acetone; a non-crystalline solid, such as an amorphous form; or a semi-solid, such as a partially solvated solid.

In some embodiments, the organic solvent of the process comprises an antisolvent in which a compound of formula (III'), e.g., compound (III), is modestly soluble. In some embodiments, the antisolvent comprises a hydrocarbon solvent, such as pentane, hexane (e.g., n-hexane or a mixture of hexane isomers), or heptane; an aromatic solvent, such as toluene, benzene, xylene (e.g., 1,2-dimethylbenzene or a mixture of xylene isomers, e.g., 1,2-dimethylbenzene, 1,3-dimethylbenzene, and/or 1,4-dimethylbenzene), cumene, or ethylbenzene; or mixtures thereof. In some preferred embodiments, the antisolvent comprises toluene.

In some embodiments, the admixture of the process comprises one or more additional organic solvents, e.g., a second organic solvent, a third organic solvent. In some embodiments, the one or more additional organic solvents comprises a non-aromatic solvent. The one or more additional organic solvents can modify the characteristics of the antisolvent, e.g., by increasing the overall polarity of the resulting admixture. In some embodiments, the non-aromatic solvent, such as ethyl acetate, is one in which the compound of formula (III'), e.g., compound (III), is dissolved prior to addition of the antisolvent.

Cooling a supersaturated solution can promote formation of crystalline compounds, such as the crystalline form of a compound of formula (III'). In some embodiments, the admixture is cooled. In some embodiments, the admixture is cooled to a range of from about −20° C. to about 25° C., such as from about −15° C. to about 15° C., about −10° C. to about 15° C., about −5° C. to about 15° C., about 0° C. to about 15° C.; such as from about −15° C. to about 10° C., about −10° C. to about 10° C., about −5° C. to about 10° C., about 0° C. to about 10° C.; such as from about −15° C. to about 5° C., about −10° C. to about 5° C., or about −5° C. to about 5° C. In some embodiments, the admixture is cooled to about −15° C., about −10° C., about −5° C., about 0° C., about 5° C., about 10° C., about 15° C., or about 20° C.

Seed crystals can provide a surface on which the crystallization process can begin. In some embodiments, the process comprises adding one or more seed crystals. In some embodiments, the one or more seed crystals comprise a compound of formula (III'), preferably the same compound of formula (III') which is the subject of the crystallization process.

Isolation of the crystalline form can comprise decanting the supernatant liquid from the admixture, or filtering the admixture to obtain the crystalline form. In some embodiments, the process comprises isolating the crystalline form of a compound of formula (III'), e.g., compound (III), by filtration. In some embodiments, the filtrate is washed with an amount of an organic solvent, e.g., the antisolvent.

In some embodiments, the process affords a crystalline compound of formula (III') that has an XRPD pattern comprising one or more, two or more, three or more, four or more, or five or more characteristic peaks expressed in degrees 2θ at about 6.1, about 12.1, about 13.1, about 18.5, and about 24.3. In some embodiments, the crystalline compound has an XRPD pattern comprising one or more, two or more, three or more, four or more, or five or more characteristic peaks expressed in degrees 2θ at 6.1±0.2, 12.1±0.2, 13.1±0.2, 18.5±0.2, and 24.3±0.2. In some embodiments, the crystalline compound has an XRPD pattern comprising the peaks as shown in Table 1. In some embodiments, the crystalline compound has an XRPD pattern substantially as shown in FIG. 3A.

In some embodiments, the process affords a crystalline compound of formula (III') that has an XRPD pattern comprising one or more, two or more, three or more, four or more, or five or more characteristic peaks expressed in degrees 2θ at about 7.3, about 10.0, about 11.6, about 17.7, and about 24.6, respectively. In some embodiments, the crystalline compound has an XRPD pattern comprising one or more, two or more, three or more, four or more, or five or more characteristic peaks expressed in degrees 2θ at 7.3±0.2, 10.0±0.2, 11.6±0.2, 17.7±0.2, and 24.6±0.2. In some embodiments, the crystalline compound has an XRPD pattern comprising the peaks as shown in Table 2A. In some embodiments, the crystalline compound has an XRPD pattern substantially as shown in FIG. 3B.

In some embodiments, the process comprises converting a first crystalline form of a compound of formula (III') to a second crystalline form of a compound of formula (III'). In an illustrative example, a first crystalline form of a compound of formula (III'), e.g., a toluene solvate of compound (III), e.g., TATD-CLE form 1, can be subjected to conditions, e.g., heated, to form a second crystalline form of a compound of formula (III'), e.g., TATD-CLE form 2. In some instances, heating a first crystal can lead to formation of a second crystal, e.g., by partially or substantially desolvating a solvate form of a first crystalline form to make a second crystalline form. Other stress conditions, such as pressurizing a first crystalline form, may also lead to formation of a second crystalline form.

6.5. Processes of Making Crystalline TATD-CLE

The synthesis of TATD-CLE is known. For example, U.S. Pat. Nos. 7,129,232 and 7,192,943 disclose a synthesis of ceftolozane and ceftolozane-like compounds, respectively, from a compound of formula (III'), e.g., compound (III) (also referred herein as TATD-CLE). The previously disclosed syntheses of TATD-CLE were based on working up reaction mixtures containing TATD-CLE with ethyl acetate or diisopropyl ether.

In contrast, disclosed herein is a synthesis of TATD-CLE using toluene. Use of toluene as a solvent for reaction isolation provides several benefits. First, the isolation with toluene provides a controlled and robust isolation process for TATD-CLE. Secondly, use of toluene in the isolation of TATD-CLE results in controlled particle size when compared to a isolation with diisopropyl ether, which produces TATD-CLE in large particles. Thirdly, small volumes of toluene solvent are used for the reaction isolation introducing an inert solvent like toluene, which will not interfere with subsequent reaction steps (i.e., inert to subsequent reaction reagents and conditions). Additionally, diisopropyl ether and related ethereal solvents can form peroxides upon storage that can be explosive. Finally, the flash point of toluene is 6° C., as compared to the flash point of diisopropyl ether of about −28° C. The higher flash point of toluene reduces the risk of fire. Thus, the use of toluene not only offers advantages with respect to the process of making TATD-CLE, but also results in unexpectedly stable, crystalline forms of TATD-CLE.

Also disclosed herein is a process to prepare a crystalline form of a compound of formula (III'), e.g., a crystalline toluene solvate of compound (III). The crystalline form of a compound confers a number of benefits, including enhanced purity of the compound, ease of compound isolation (e.g., ease of filtering), and enhanced stability as compared with a non-crystalline form (e.g., to degradation by, e.g., heat, light, radiation, undesirable chemical side reactions), which allows for long-term storage.

Figure 2:
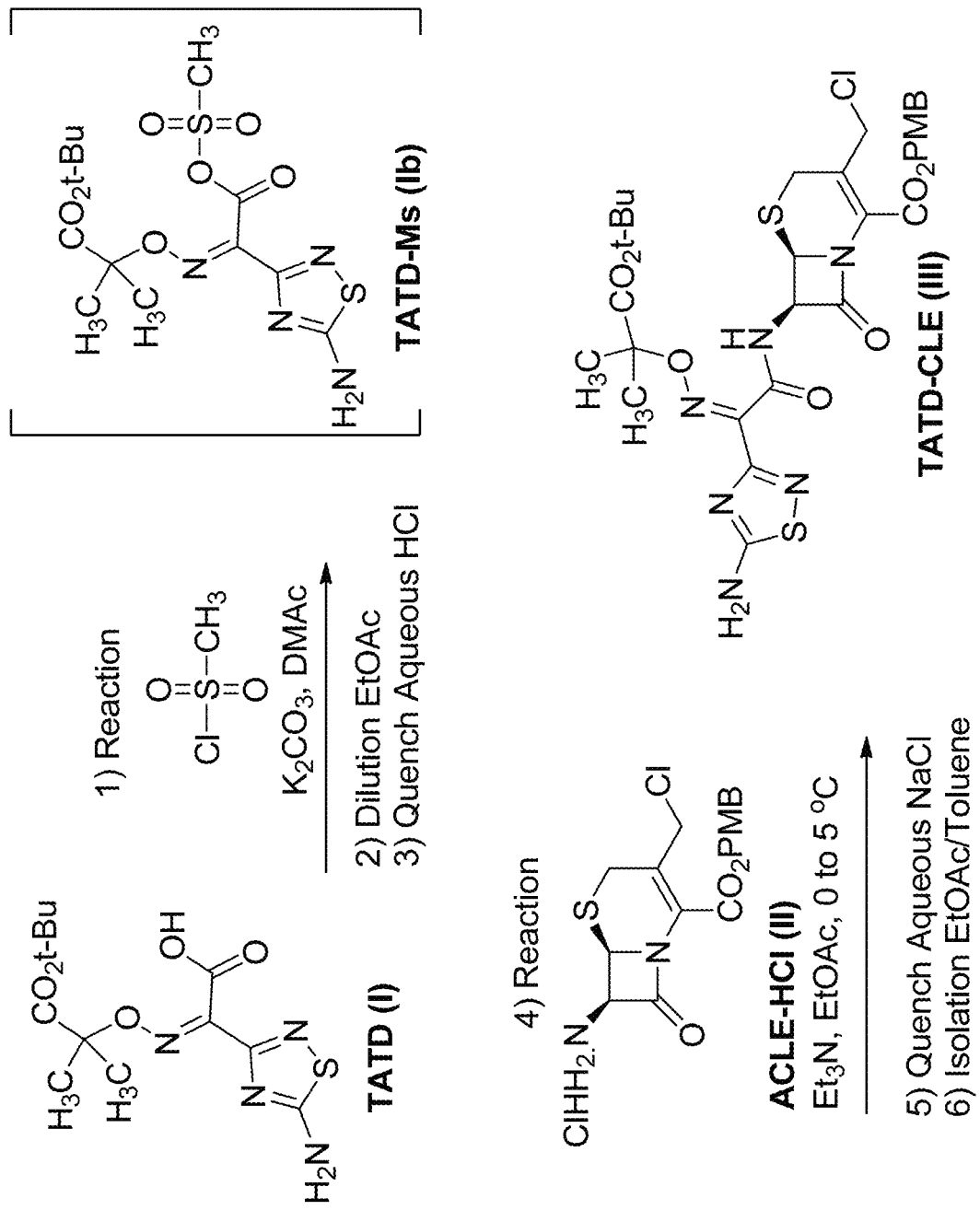
FIG. 2 is a synthetic scheme for preparing a toluene solvate of compound (III) (TATD-CLE) from TATD-Ms (compound (Ib)) via reaction with ACLE (compound (II)).

As a non-limiting example, forms of a crystalline compound of formula (III'), e.g., TATD-CLE toluene solvate, can be prepared from the reaction illustrated in FIG. 2, wherein ACLE-HCl, a compound of formula (II), (also known as (6R,7R)-3-(chloromethyl)-2-(((4-methoxybenzyl)oxy)carbonyl)-8-oxo-5-thia-1-azabicyclo[4.2.0]oct-2-en-7-aminium chloride with CAS No.: 113479-65-5) is admixed, e.g., reacted, with TATD-Ms, a compound of formula (Ib). This conversion of TATD-Ms to TATD-CLE can be carried out in the presence of triethylamine. In an embodiment, the reaction of ACLE-HCl, a compound of formula (II), with TATD-Ms, a compound of formula (Ib), is carried out over about 1 hour of reaction time in solution, preferably in a biphasic solvent mixture such as ethyl acetate and water, at a temperature of from about 0° C. to about 7° C. and pH of from about 2 to about 4. In an embodiment, the pH is adjusted by using triethylamine ($Et_3N$).

In an embodiment, the process of obtaining the toluene solvate of TATD-CLE further comprises obtaining compound (III) by adding sodium chloride solution to the reaction mixture of compound (II) and compound (Ib), followed by separation of the aqueous layer from the organic layer (e.g., the ethyl acetate layer) and further washing the organic layer with sodium chloride solution.

Formation of the crystalline compound of formula (III'), e.g., TATD-CLE, e.g., the toluene solvate, can comprise extracting TATD-CLE from the reaction mixture with a first organic solvent and concentrating the first organic extract, followed by addition of an antisolvent, e.g., toluene, to the first organic extract. Isolation of the solids by filtering, and washing the filtered solids with antisolvent, e.g., toluene, can yield the crystalline TATD-CLE, e.g., toluene solvate, as a solid after drying. In an embodiment, the first organic solvent comprises ethyl acetate.

FIG. 2 and Table 3 provide exemplary ranges of values for various process parameters (Step 4, Step 5, Step 6) for the manufacturing of solid forms of TATD-CLE, e.g., the toluene solvate, as well as preferred ranges and values for each process parameter.

TABLE 3

Process Parameters for the Formation and Isolation of TATD-CLE Solid Forms

| Process Parameter | Preferred Range | Normal Operating Range | Target Value |
|---|---|---|---|
| (Step 4) Process Parameters for the Reaction to Form TATD-CLE | | | |
| Water (vol., L/kg) | ≥2 | 2 to 5 | 3 |
| EtOAc (vol., L/kg) | ≥2 | 2 to 5 | 3 |
| Reaction pH | 2.0 to 5.0 | 2.0 to 4.0 | 3.5 |
| Reaction temperature (° C.) | 0 to 10 | 0 to 7 | 2 |
| (Step 5) Process Parameters for the Quench of TATD-CLE | | | |
| Temperature of quench (° C.) | −10 to 20 | −5 to 5 | 0 |
| NaCl (wt. equiv) | 0.0 to 0.2 | 0.05 to 0.15 | 0.10 |
| NaCl solution concentration (w/v %) | 5 to 25 | 18 to 22 | 20 |
| NaCl solution (vol., L/kg) | ≥2 | 2 to 4 | 3 |
| (Step 6) Process Parameters for the Isolation of TATD-CLE | | | |
| Distillation temperature (° C.) | ≤30 | 15 to 25 | 20 |
| Batch volume after concentration (vol., L/kg) | 2.5 to 3.5 | 2.5 to 3.5 | 3.0 |
| Temperature before cooling (° C.) | 10 to 30 | 18 to 22 | 20 |
| $1^{st}$ toluene portion (vol., L/kg) | 0.5 to 2.0 | 0.5 to 1.5 | 1.0 |
| Seed amount (weight %) | 0.5 to 8.0 | 3.0 to 5.0 | 4.0 |
| Batch stirring time after seed (h) | 1 to 8 | 2 to 4 | 3 |
| $2^{nd}$ toluene portion (vol., L/kg) | 6 to 16 | 8 to 10 | 9 |
| $2^{nd}$ toluene addition rate (vol./h) | 0.3 to 3 | 0.4 to 1 | 0.5 |
| Batch stirring time before cooling (h) | ≥1 | 3 to 5 | 4 |
| Temperature during cooling (° C.) | −10 to 30 | 0 to 10 | 1 |
| Toluene product wash (vol., L/kg) | ≥1 | 2 to 10 | 8 |

A composition comprising a crystalline compound of formula (III'), e.g., TATD-CLE toluene solvate, can be obtained by a process comprising the conditions described in Table 3: (Step 4) Process Parameters for the Reaction to Form TATD-CLE; (Step 5) Process Parameters for the Quench of TATD-CLE; and (Step 6) Process Parameters for the Isolation of TATD-CLE.

The reaction to form TATD-CLE (Step 4, Table 3) comprises the steps of: (a) forming a reaction mixture comprising ACLE-HCl, water (from about 2 to about 5 volumes), and EtOAc (from about 2 to about 5 volumes); (b) adjusting the pH of the reaction mixture to between about 2 and about 4 with triethylamine ($Et_3N$); (c) adding compound (Ib) (TATD-Ms) in EtOAc to the reaction mixture, while maintaining a pH of between about 2 and about 4 with additional $Et_3N$; (d) agitating the reaction mixture until the reaction is complete (i.e., until residual levels of ACLE are <2.2% (area % on HPLC) with respect to TATD-CLE.

In an embodiment, the time sufficient for completion of the reaction is between about 0.5 and about 1 hour. In another embodiment, a reaction temperature of from about 0 to about 7° C. is maintained throughout the reaction.

The procedure to quench the reaction resulting in TATD-CLE (Step 5, Table 3) comprises the steps of: (a) adjusting the reaction mixture to a temperature of from about −5 to about 5° C.; (b) adding from about 0.05 to about 0.15 weight equivalents of solid NaCl to the reaction mixture, then agitating and allowing separation of the mixture into an aqueous phase and an organic phase; (c) removing the aqueous phase and adding from about 18 to about 22 (w/v %) of aqueous NaCl to the remaining organic phase; (d) adding from about 2 to about 4 volumes of NaCl solution to the mixture; (e) agitating the mixture, allowing the mixture to separate into an aqueous phase and an organic phase, and isolating the organic phase.

The procedure to make the crystalline compound of compound (III), i.e., "isolation of TATD-CLE solid form" shown in Table 3 above, comprises the steps of one or more of the following: (a) concentrating the organic phase comprising the TATD-CLE (described above in Step 5(e)) to from about 2.5 to about 3.5 volumes under reduced pressure, at a temperature between about 15 and about 25° C.; (b) (1) adding a first portion of an aromatic solvent, e.g., toluene, (from about 0.5 to about 1.5 volumes) and, optionally, (2) seeding with TATD-CLE (from about 3 to about 5 weight %); (c) stirring the mixture of step (b) until nucleation (i.e., further crystal formation) occurs; (d) (1) adding a second portion of the aromatic solvent, e.g., toluene, (from about 8 to about 10 volumes) at a rate of from about 0.4 to about 1 volumes/hour, (2) stirring the resulting suspension for from about 3 to about 5 hours, (3) optionally, cooling to from about 0 to about 10° C., and (4) isolating, e.g., filtering, the precipitate (i.e., crystals); (e) washing the isolate, e.g., filter cake, with toluene (from about 2 to about 10 volumes), and (f) drying the isolate, e.g., filter cake, e.g., under reduced pressure.

In one embodiment, the filter cake (i.e., comprising the crystalline compound of formula (III')) is dried with a nitrogen flow until the water content is ≤0.7% (IPC-3) and a LOD of ≤14.5% (IPC-4) denoting completion of the drying process. In another embodiment, a typical drying time is from about 8 to about 24 hours.

In one embodiment, the time sufficient for nucleation to occur is from about 2 to about 4 hours.

In an aspect, provided herein is process of making a toluene solvate of compound (III):

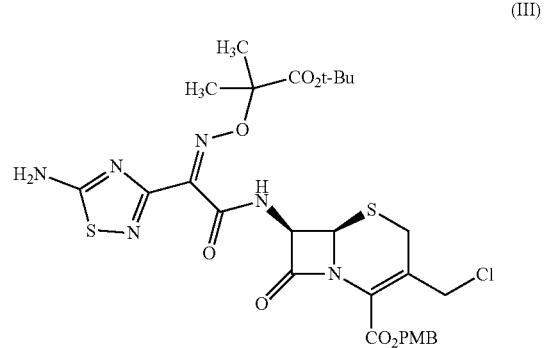

(III)

comprising the steps of:
(a) admixing, e.g., reacting, compound (II):

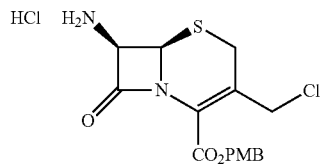
(II)

with compound (Ib):

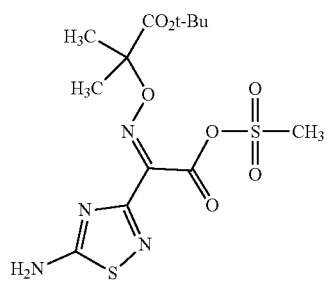
(Ib)

to form compound (III); and
(b) admixing, e.g., extracting, compound (III) with an organic solvent comprising toluene; to obtain the toluene solvate of compound (III).

In an embodiment, the process further comprises the synthesis of compound (Ib):

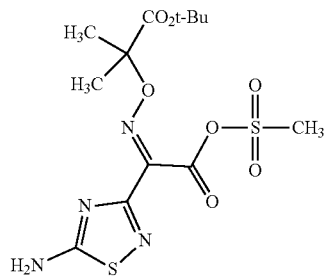
(Ib)

by a process comprising the step of admixing, e.g., reacting, compound (I)

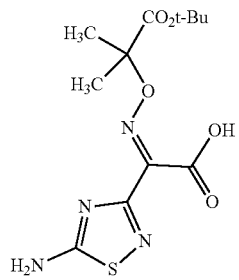
(I)

with methanesulfonyl chloride and potassium carbonate to yield compound (Ib).

In an aspect, provided herein is process of making a toluene solvate of compound (III):

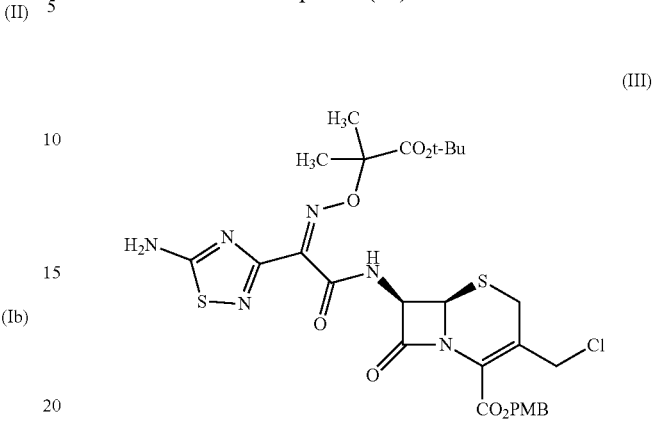
(III)

comprising the steps of admixing compound (III) with an organic solvent comprising toluene to obtain the toluene solvate of compound (III).

In an embodiment, the toluene solvate is crystalline. In a further embodiment, the toluene solvate has an X-ray powder diffraction pattern comprising one or more, two or more, three or more, four or more, or five or more characteristic peaks expressed in degrees 2θ at about 6.1, about 12.1, about 13.1, about 18.5, and about 24.3.

6.6. Processes Using a Crystalline Form of a Compound of Formula (III')

Disclosed herein are processes for using a crystalline form of a compound of formula (III'), e.g., compound (III), which can be used to synthesize other organic compounds.

In some embodiments, a process of making a compound of formula (V'), or a pharmaceutically acceptable salt thereof:

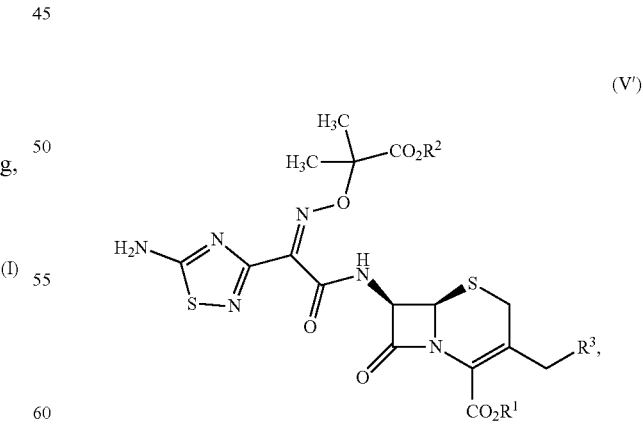
(V')

wherein $R^3$ is selected from the group consisting of —COOH, —OH, an alkoxy, a urea, a nitrogen-containing heteroaryl and a nitrogen-containing heterocyclyl, wherein said alkoxy, nitrogen-containing heteroaryl and nitrogen-containing heterocyclyl are each optionally substituted;

comprises the step of admixing a crystalline form of a compound of formula (III'):

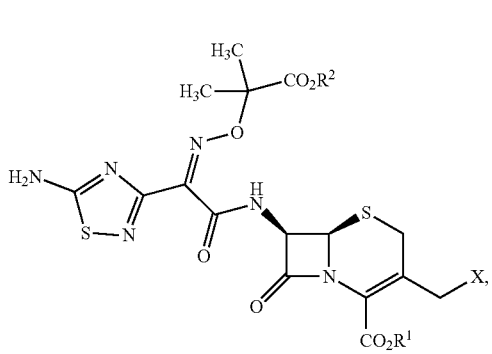

(III')

wherein X is Cl, Br, or I; and $R^1$ and $R^2$ are each independently an oxygen protecting group; with a nucleophile ($R^3$-M), wherein M is H, a metal cation, a non-metal cation, or lone pair of electrons; to form a compound of formula (V').

M can be a metal selected from, for example, alkali metals, alkaline earth metals, transition metals, and main group metals. For metal cations having a formal charge greater than one (e.g., 2), more than one equivalent of $R^3$ will be present in the nucleophile (e.g., $(R^3)_2M$).

One skilled in the art will recognize that the formal charge of $R^3$ changes when a lone pair reacts to form a bond.

In some embodiments, M is H, a metal cation or a non-metal cation, e.g., an ammonium cation, and $R^3$ is selected from the group consisting of:

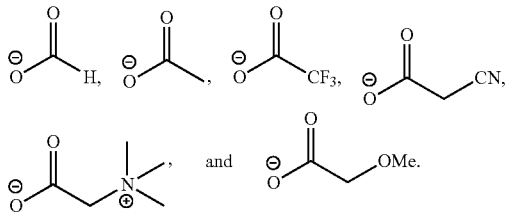

In some embodiments, M is H and $R^3$-M is selected from the group consisting of

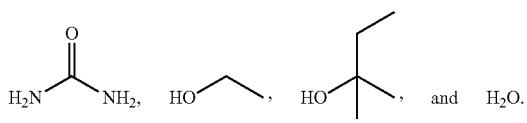

In some embodiments, $R^3$ is a nitrogen-containing heteroaryl (i.e., nitrogen-containing heteroaryl, or a heteroaryl containing at least one nitrogen in the ring). Nitrogen-containing heteroaryls include but are not limited to pyrazoles, pyrroles, triazoles, pyridines, pyrimidines, thiazoles, and thiadiazoles, each of which can be optionally substituted. In some embodiments, $R^3$ is a pyrazole, pyrrole, triazole, or pyridine, which are each optionally substituted. In some embodiments, $R^3$ is a pyrazole or a pyridine, which are each optionally substituted. In some embodiments, $R^3$ is an unsubstituted pyridine.

In some embodiments, $R^3$-M is a compound of formula (IV'):

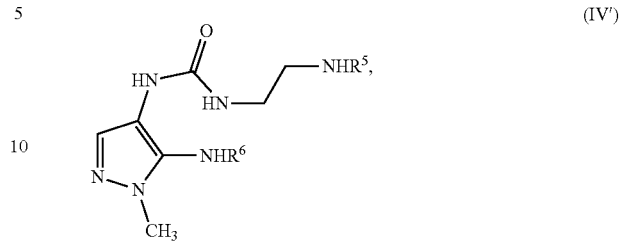

(IV')

wherein $R^5$ and $R^6$ are each independently a nitrogen protecting group.

In some embodiments, $R^5$ and $R^6$ are each independently an acid-labile nitrogen protecting group. In some embodiments, $R^5$ and $R^6$ are each independently selected from the group consisting of: triphenylmethyl, tert-butoxycarbonyl, 2-trimethylsilylethoxycarbonyl, or triphenylmethyl.

In some embodiments, $R^5$ is tert-butoxycarbonyl.

In some embodiments, $R^6$ is triphenylmethyl.

In some embodiments, the compound of formula (IV') has the structure of compound (IV):

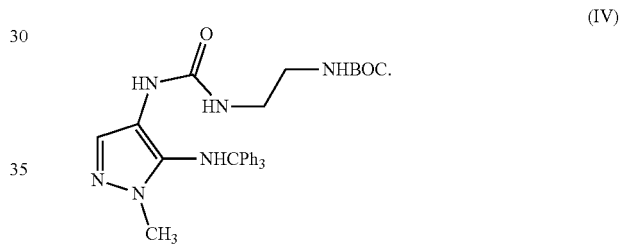

(IV)

In some preferred embodiments, a compound of formula (V'), or a pharmaceutically acceptable salt thereof, has the structure of formula (V''):

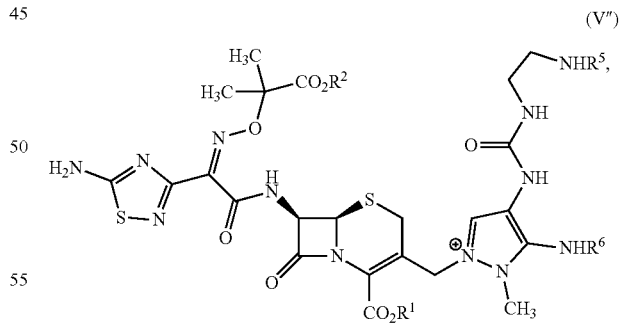

(V'')

wherein $R^5$ and $R^6$ are as defined herein, and $A^\ominus$ is a pharmaceutically acceptable anion.

In some embodiments, $A^\ominus$ is chloride, bromide, iodide, sulfate, bisulfate, tosylate (i.e., toluenesulfonate), mesylate (i.e., methanesulfonate), edisylate, maleate, phosphate (e.g., monophosphate, biphosphate), ketoglutarate, trifluoroacetate, or triflate (i.e., trifluoromethanesulfonate). In some embodiments, $A^\ominus$ is chloride, bromide, iodide, sulfate, bisulfate, tosylate, mesylate, trifluoroacetate, or triflate. In certain embodiments, $A^\ominus$ is selected from chloride, acetate, trifluoroacetate and bisulfate (i.e., hydrogen sulfate). In a particular embodiment, $A^\ominus$ is trifluoroacetate or bisulfate (i.e., $HSO_4^-$). In certain embodiments, $A^\ominus$ is trifluoroacetate. In certain embodiments, $A^\ominus$ is bisulfate.

In some preferred embodiments, the compound of formula (V") and/or formula (V') has the structure of a compound of formula (V) ("compound (V)"):

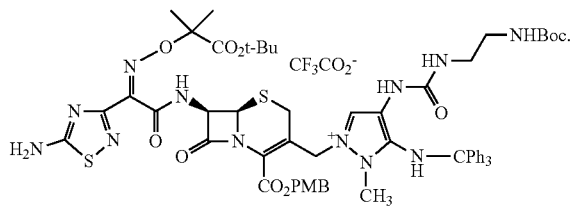

(V)

In some embodiments, the process comprises the step of converting a compound of formula (V'), e.g., a compound of formula (V") and/or compound (V), to compound (VI'):

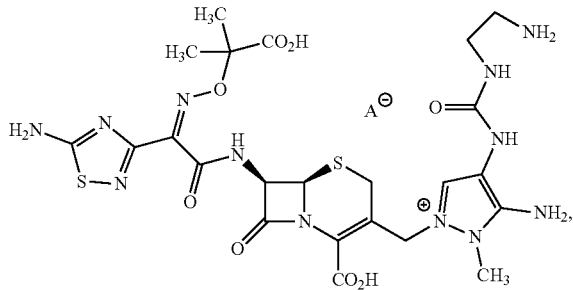

(VI')

wherein $A^\ominus$ is as defined herein.

In some embodiments, the compound of formula (VI') has the structure of compound (VI):

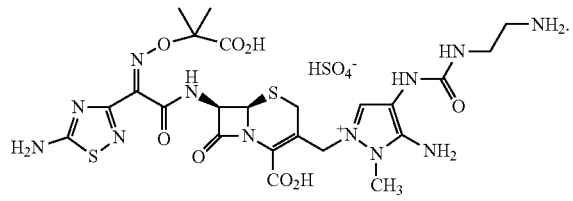

(VI)

In some embodiments, the step of converting a compound of formula (V') to a compound of formula (VI'), e.g., compound (VI), comprises exposing, e.g., contacting, the compound of formula (V') to a strong acid, e.g., trifluoroacetic acid.

In some embodiments, the process comprises the step of converting a compound of formula (VI') to compound (VI), comprising contacting the compound of formula (VI') with sulfuric acid.

Figure 1B:
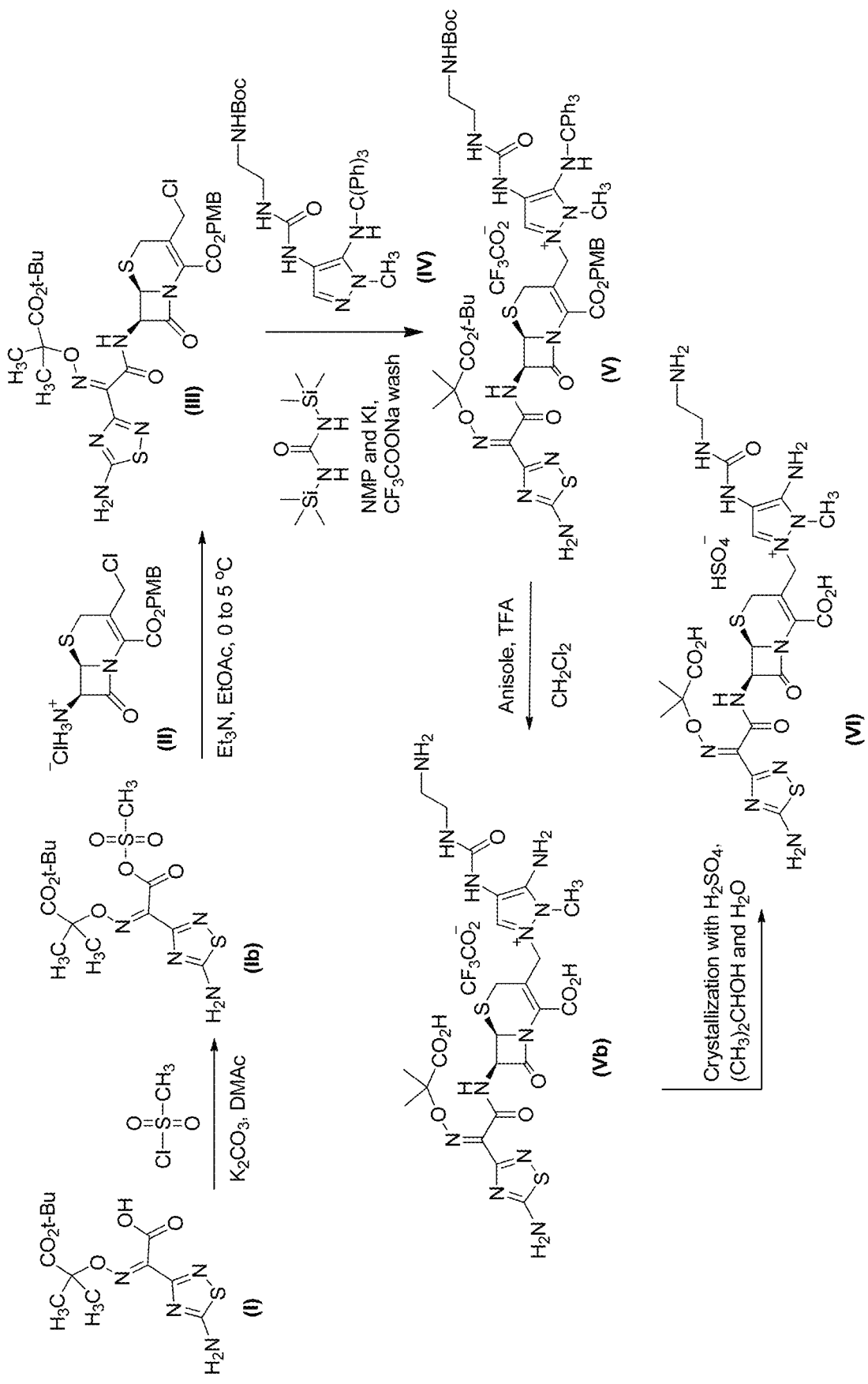
Figure 1C:
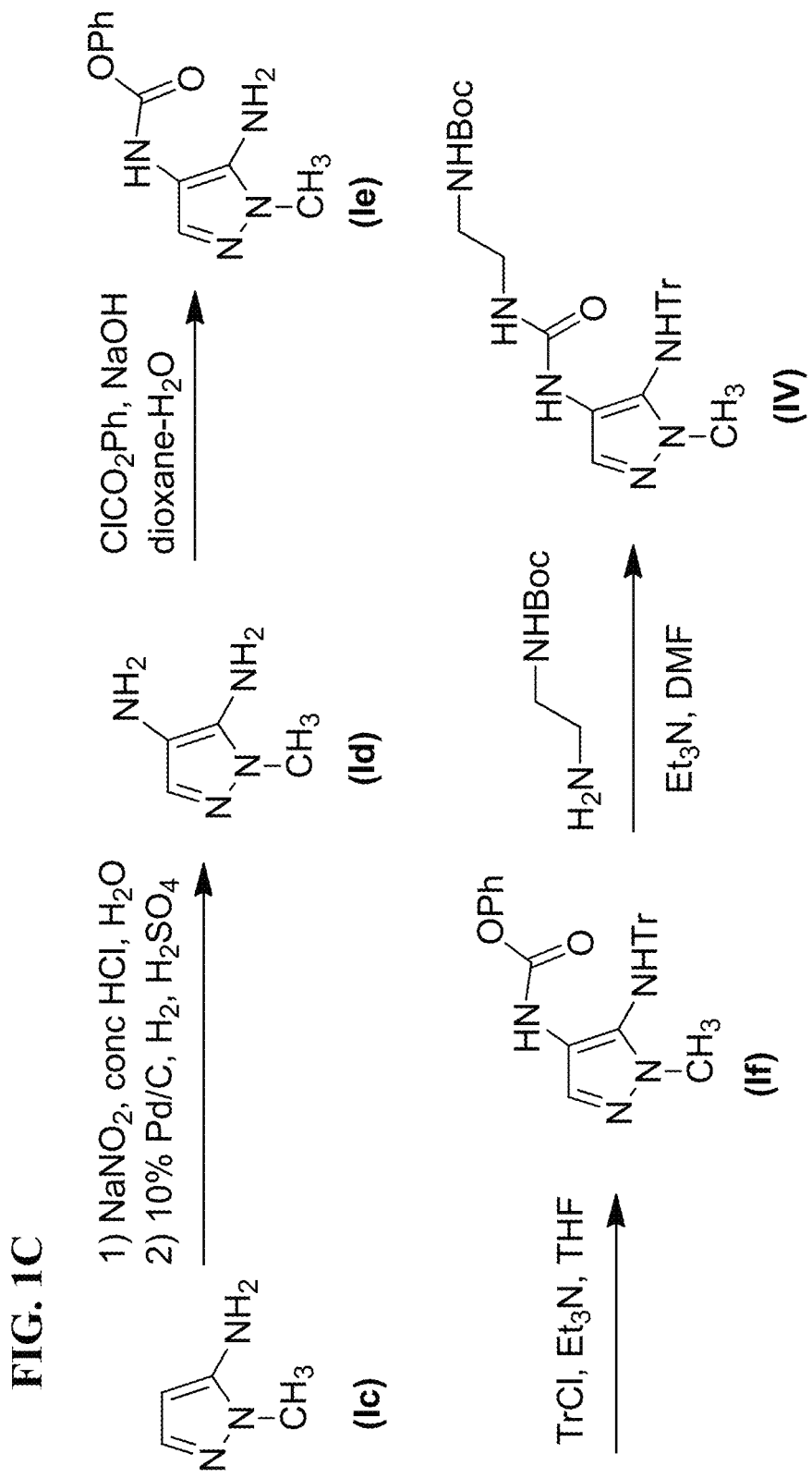

6.7. Crystalline TATD-CLE (e.g., Toluene Solvate) in the Synthesis of Cephalosporins Ceftolozane can be obtained using methods described in U.S. Pat. Nos. 7,129,232 and 7,192,943, as well as Toda et al., "Synthesis and SAR of novel parenteral antipseudomonal cephalosporins: Discovery of FR264205," *Bioorganic & Medicinal Chemistry Letters*, 18, 4849-4852 (2008). Referring to FIGS. 1B and 1C, the synthesis of ceftolozane was disclosed from the starting material thiadiazolyl-oximinoacetic acid derivative (compound (I)), also referred to as TATD. Activation of carboxylic acid group of thiadiazolyl-oximinoacetic acid derivative (compound (I)) is carried out by methanesulfonyl chloride and potassium carbonate in a conventional solvent such as N,N-dimethylacetamide to yield the activated thiadiazolyl-oximinoacetic acid methane sulfonate ester (Ib). The reaction of activated thiadiazolyl-oximinoacetic acid derivative (compound (Ib)) and 7-aminocephem compound (II) is disclosed to obtain compound (III), which can be further reacted with 4-[(N-Boc-aminoethyl)carbamoylamino]-1-methyl-5-tritylamino-pyrazole (IV) to obtain ceftolozane intermediate compound (V). The ceftolozane intermediate (compound (V)) is universally deprotected using a mixture of trifluoroacetic acid (TFA) and anisole to yield ceftolozane TFA intermediate compound (Vb), which is further crystallized with sulfuric acid to afford ceftolozane sulfate (compound (VI)).

The current invention offers several benefits to the synthesis of ceftolozane using TATD-CLE toluene solvate. For example, it provides a crystalline TATD-CLE product which contains low amounts of impurities due to the crystalline nature of the compound.

In an aspect, provided herein is a process of making a compound of formula (V):

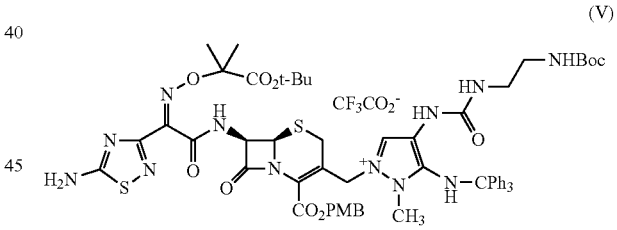

(V)

comprising the step of admixing, e.g., reacting, a toluene solvate of compound (III):

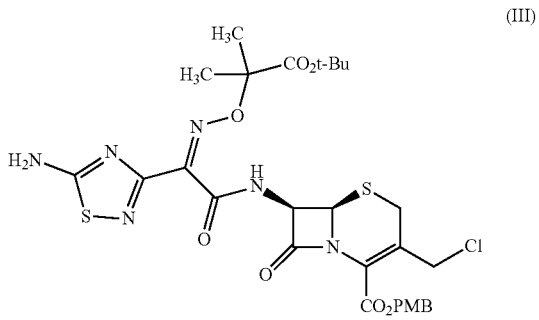

(III)

with compound (IV):

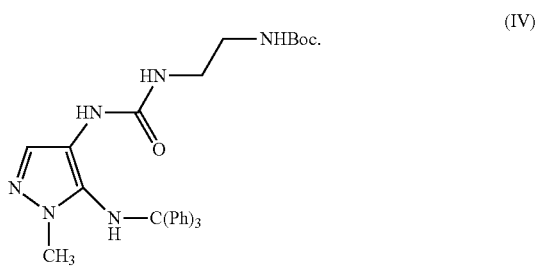

In an embodiment, the process further comprises the step of converting compound (V):

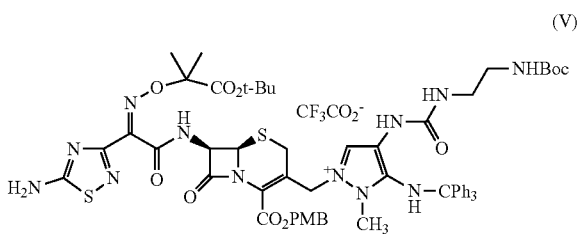

to compound (VI):

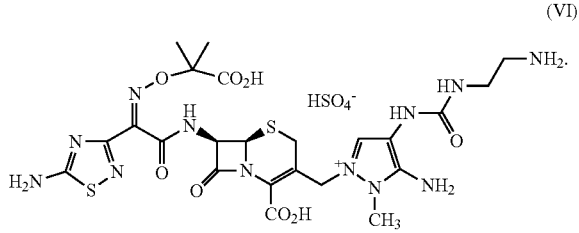 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; "HSO4-"]

In one embodiment, the step of converting compound (V) to compound (VI) comprises exposing compound (V) to, e.g., contacting with, a strong acid, such as trifluoroacetic acid, sulfuric acid, formic acid, hydrochloric acid, or mixtures thereof. In some embodiments, the step further comprises removing the excess strong acid. In some embodiments, the step comprises contacting with more than one strong acid, simultaneously (i.e., in a mixture) or consecutively (e.g., trifluoroacetic acid, concentration of the solution, then contacting with sulfuric acid).

In another aspect, provided herein is a cephalosporin compound, wherein the compound is prepared from a toluene solvate of compound (III) via the synthetic processes described herein (e.g., FIG. 1B).

6.8. Pharmaceutical Compositions

Ceftolozane (i.e., a compound of formula (Va), including pharmaceutically acceptable salts thereof such as ceftolozane sulfate) can be formulated as a pharmaceutical composition. The pharmaceutical composition can optionally further include a beta-lactamase inhibitor such as tazobactam. The ceftolozane can be obtained by processes described herein. In particular, pharmaceutical compositions can be obtained by a process comprising the step of forming an aqueous solution containing ceftolozane, and lyophilizing the aqueous solution to obtain a pharmaceutical composition. The aqueous solution may additionally comprise excipients, stabilizers, pH adjusting additives (e.g., buffers) and the like. Non-limiting examples of these additives include sodium chloride, citric acid and L-arginine For example, the use of sodium chloride can result in greater stability; L-arginine can be used to adjust pH and to increase the solubility of ceftolozane; and citric acid can be used to prevent discoloration of the product, due to its ability to chelate metal ions. In particular, the aqueous solution can include ceftolozane sulfate and additional components such as sodium chloride to stabilize the ceftolozane, and an alkalizing agent such as L-arginine to provide a pH of about 5-7 prior to lyophilization. The pharmaceutical compositions can be lyophilized (freeze-dried) and stored as a lyophilate for later reconstitution. Exemplary disclosures relating to lyophilization of pharmaceutical formulations include Konan et al., Int. J. Pharm. 2002, 233 (1-2), 293-52; Quintanar-Guerrero et al., J. Microencapsulation 1998, 15 (1), 107-119; Johnson et al., J. Pharmaceutical Sci. 2002, 91 (4), 914-922; and Tang et al., Pharmaceutical Res. 2004, 21 (4), 191-200; the disclosures of which are incorporated herein by reference. As an alternative to lyophilization, a pharmaceutical composition can be spray dried, or stored frozen and then thawed, reconstituted, and diluted before administration.

Pharmaceutical compositions can include ceftolozane obtained by methods described herein, combined with a beta-lactamase inhibitor, such as tazobactam (CAS#: 89786-04-9), avibactam (CAS# 1192500-31-4), Sulbactam (CAS# 68373-14-8) and/or clavulanate (CAS# 58001-44-8). The beta lactamase inhibitor can be included in a crystalline or amorphous form, such as a lyophilized tazobactam or crystalline tazobactam (e.g., U.S. Pat. Nos. 8,476,425 and 5,763,603) to obtain the pharmaceutical composition.

Pharmaceutical compositions comprising ceftolozane can be formulated to treat infections by parenteral administration (including subcutaneous, intramuscular, and intravenous) administration. In one particular embodiment, the pharmaceutical compositions described herein are formulated for administration by intravenous injection or infusion. Pharmaceutical antibiotic compositions can include ceftolozane sulfate and stabilizing amount of sodium chloride (e.g., 125 to 500 mg of sodium chloride per 1,000 mg ceftolozane active) in a lyophilized unit dosage form (e.g., powder in a vial). The unit dosage form can be dissolved with a pharmaceutically acceptable carrier, and then intravenously administered. In another aspect, pharmaceutical antibiotic compositions can include ceftolozane sulfate obtained by a process comprising the steps of lyophilizing an aqueous solution containing ceftolozane and a stabilizing amount of sodium chloride, where the stabilizing amount of sodium chloride is from about 125 to about 500 mg of sodium chloride per 1,000 mg ceftolozane active in the aqueous solution prior to lyophilization.

6.9. Methods of Treatment

In one aspect, provided herein is a method for the treatment of bacterial infections in a mammal, comprising administering to said mammal a therapeutically effective amount of a pharmaceutical composition comprising ceftolozane, or a pharmaceutically acceptable salt thereof, prepared according to one or more of the methods described herein. A method for the treatment of bacterial infections in a mammal can comprise administering to said mammal a therapeutically effective amount of a pharmaceutical composition comprising ceftolozane sulfate and sodium chloride.

The pharmaceutical compositions can used in combination with metronidazole for the treatment of complicated intra-abdominal infections caused by the following Gram-negative and Gram-positive microorganisms such as: *Escherichia coli* (including strains producing CTX-M-14/15 ESBLs), *Klebsiella pneumoniae* (including strains producing CTX-M-15 ESBLs), *Pseudomonas aeruginosa, Enterobacter cloacae, Klebsiella oxytoca, Proteus mirabilis, Bacteroides fragilis, Bacteroides ovatus, Bacteroides thetaiotaomicron, Bacteroides vulgatus, Streptococcus anginosus, Streptococcus constellatus,* and *Streptococcus salivarius.*

The pharmaceutical compositions can used for the treatment of complicated urinary tract infections, including pyelonephritis, with or without concurrent bacteremia, caused by the following Gram-negative microorganisms: *Escherichia coli* (including strains resistant to levofloxacin and/or producing CTX-M-14/15 ESBLs), *Klebsiella pneumoniae* (including strains resistant to levofloxacin and/or producing CTX-M-15 ESBLs), *Proteus mirabilis,* and *Pseudomonas aeruginosa.*

The recommended dosage regimen of pharmaceutical compositions comprising ceftolozane prepared by one or more methods disclosed herein, and tazobactam in an amount providing 1 g of ceftolozane active per 500 mg of tazobactam acid, is 1.5 g administered every 8 hours by intravenous (IV) infusion over 1 hour in patients≥18 years of age. The duration of therapy should be guided by the severity and site of infection and the patient's clinical and bacteriological progress (e.g., every 8 hours for 4-14 days for complicated Intra-Abdominal Infections and 7 days for Complicated Urinary Tract Infections, including Pyelonephritis).

7. EXAMPLES

7.1. Instrumentation and Methods

Other than Comparative Example 2, and unless otherwise indicated, the following instrumentation and methods were used in the working Examples described herein. Comparative Example 2 was reported in U.S. Pat. No. 7,192,943.

7.1.1. X-ray Powder Diffraction (XRPD)

X-ray Powder Diffraction experiments were performed on a Bruker D8 diffractometer using Cu Kα radiation (40 kV, 40mA), θ- 2θ goniometer, primary and secondary Soller slits) (2.5°), and a Ge monochromator and Lynxeye detector (opening angle of 2.948°). Certified Corundum standard (NIST 1976) was used to check the performance of the instrument. Data collection was performed by Diffrac. Suite Measurement Center v2.2.47.1 and the collected data was analyzed and presented using Diffrac.EVA v2.0 or v3.0.

Samples were tested under ambient conditions unless otherwise indicated. Approximately 5 mgs of each sample was flattened onto the zero-background silicon wafer, resulting in a smooth and flat surface. The scan type of coupled two theta/theta was used for the data collection. The angular range used was 5 to 40 °2θ, and the step size was 0.020 °2θ. The collection time was 0.1 s for each step. The geniometer radius was set at 280 mm. The sample rotation speed was 15 rpm, and the slit size used was 0.6 mm.

Reflections above 1% relative intensity are reported.

7.1.2. Variable Temperature (VT)-XRPD

Approximately 40 mg of the sample was placed in a Ni-coated sample holder under ambient conditions. The sample was placed in Anton-Paar TTK 450 chamber at 25° C. The temperature was controlled in-situ through the measurement. The sample was heated from 30° C. to 170° C. at 2° C./min. XRPD data were collected at specific temperatures for 25 min per data collection.

7.1.3. Thermal Analysis

Thermogravimetric Analysis (TGA) experiments were performed on a TA Instruments Discovery Series TGA. The calibration for temperature was carried out using certified indium. Typically, 3-15 mg of a sample was flattened into sealed aluminum pans. Data was acquired for samples with and without a pinhole. For samples with a pinhole, once crimped and sealed, the auto-sampler punched the lid of the sample with its internal puncher right before analysis of the sample. Samples were heated at 20° C./min from 30° C. to 400° C. Dry nitrogen was purged into the system during the experiment at a rate of 50 mL/min. The software used to control the instrument was TRIOS Explorer Software v5.3.0.75. TRIOS software v2.40.1838 or v2.04.04563 was used for data analysis.

Differential Scanning Calorimetry (DSC) experiments were performed on a TA Instruments Q2000. The calibration for thermal capacity was carried out using sapphire and the calibration for energy and temperature was carried out using certified indium. Typically, 3-10 mg of a sample is flattened into sealed aluminum hermetic pans and the weight accurately recorded. Data was acquired for samples with a pinhole in the lid. Samples were heated at 10° C./min from 25° C. to 350° C. Dry nitrogen was purged into the system during the experiment at a rate of 50 mL/min. The software used to control the instrument is the Advantage for Q Series v2.9.0.396 and the Thermal Advantage v5.4.0. Data was analyzed using the Universal Analysis v4.5A software.

7.1.4. Residual Solvent (Toluene) Analysis

TATD-CLE was analyzed for toluene by gas chromatography using an Agilent 6890 gas chromatograph coupled with a flame-ionization detector. Headspace sampler Agilent 7694 was used to deliver the sample to the gas chromatography (GC) column. Details of the method are described below.

7.1.4.1. Standard Preparation

Linearity standard solutions of toluene were prepared in dimethyl sulfoxide (2 mL total volume in headspace vial) with final standard amounts of 310.7 µg, 512.2 µg, 1280 µg, 1536 µg, 2049 µg, 4097 µg, and 5122 µg. For the TATD-CLE sample size of approximately 10 mg, these toluene standard amounts are equivalent to w/w 3.11%, 5.12%, 12.8%, 15.36%, 20.49%, 40.97%, and 51.22%, respectively.

7.1.4.2. Sample Preparation

TATD-CLE solid was equilibrated to room temperature. Into a 20-mL headspace vial, approximately 11 mg of TATD-CLE was accurately weighed and dissolved in 2 mL of dimethyl sulfoxide. Two additional sample solutions were prepared in the identical fashion using separate weighings of TATD-CLE. Matrix spike samples were prepared in triplicate with toluene spiking amount equivalent to 1294 µg in approximately 11 mg of TATD-CLE. These matrix spike samples were analyzed to demonstrate accuracy of the method via determination of percent recovery.

Samples and standards were analyzed using the analytical method conditions described in Table 4. Retention time for toluene under these method conditions was approximately 12.8 minutes. Toluene peak area values corresponding to the linearity standard amounts were calibrated against these standard amounts to generate a calibration curve. The amount of toluene in each of the three samples was determined using equation 1. The weight by weight value of toluene relative to TATD-CLE (compound (III)) was determined using equation 2. Toluene content in TATD-CLE (compound (III)) was reported as the mean of the triplicate values.

$$W_{Toluene}(\text{in } \mu g) = \frac{A_{Toluene} - b}{m} \quad \text{(equation 1)}$$

Where, $W_{Toluene}$=Amount of toluene in μg
$A_{Toluene}$=GC Peak area for toluene
b=intercept of the calibration curve
m=slope of the calibration curve $$\text{Toluene (\%)} = \frac{W_{Toluene}}{W_{TATO-CLE}} \times \frac{1}{10000} \quad \text{(equation 2)}$$

Where, $W_{Toluene}$=Amount of toluene (μg) determined using equation 1
$W_{TATD-CLE}$=Weight of TATD-CLE (g)
10000=factor to convert parts per million to percent

TABLE 4

| Gas Chromatographic and Headspace Sampler Conditions | | | |
|---|---|---|---|
| GC Column | Rxi-624 Sil MS, 320 μm × 30 m, 1.8 μm thickness (Restek Corporation) | | |
| GC Parameters | | | |
| Carrier Gas | Helium | | |
| Flow Rate | 0.9 mL/min | | |
| Column Temperature (ramp) | Initial | 40° C. | |
| | 6.00 min | 40° C. | |
| | 12.75 min | 180° C. | |
| | 15.00 min | 180° C. | |
| | 18.00 min | 300° C. | |
| Inlet Temperature | 200° C. | | |
| Detector Temperature | 240° C. | | |
| Split Ratio | 1:1 | | |
| Injection Volume | Full Loop (1 mL) | | |
| Run Time | 18 minutes | | |
| Detector Flow Rates | Hydrogen | 35 mL/min | |
| | Make up | 25 mL/min | |
| | Air | 350 mL/min | |
| Headspace Sampler Parameters | | | |
| Vial Temperature | 90° C. | | |
| Loop Temperature | 105° C. | | |
| Transfer Line Temperature | 125° C. | | |
| GC Cycle Time | 24 min | | |
| Thermostat Time | 20 min | | |
| Vial Pressure | 0.75 bar | | |
| Vial Pressurization Time | 0.5 min | | |
| Loop Fill Time | 0.5 min | | |
| Loop Equilibration Time | 0.1 min | | |
| Inject Time | 1.00 min | | |
| Carrier Pressure | 1.80 bar | | |

7.1.4.3. System Suitability

A resolution solution comprising solvents methanol, ethanol, isobutanol, acetone, acetonitrile, methylene chloride, methyl t-butyl ether, ethyl acetate, benzene, tetrahydrofuran, heptane, toluene, anisole, triethylamine, and pyridine, prepared in dimethyl sulfoxide diluent, was injected along with appropriate diluent blanks to demonstrate analyte specificity and resolution. Check standards were prepared at the 1553 μg toluene level, which is the mid-point level of the calibration standard range. These check standards were injected after every 10 injections. The sequence dataset was considered valid as the correlation coefficient ($r^2$) of the calibration curve was greater than 0.995, the independent check standards agreed with initial calibration curve within ±10%, and the percent recovery of toluene in the matrix spike samples were within the range of 90% -110%.

7.1.5. NMR method

NMR experiments were performed on a 400 MHz Bruker Avance HD NMR (Nuclear Magnetic Resonance) Spectrometer equipped with a 5 mm PABBO/$^{19}$F-$^{1}$H/D probe. The sample was prepared by dissolving 13 mg of TATD-CLE toluene solvate compound (III) into 1 mL CDCl$_3$. The solution was transferred into a 5-mm NMR tube and the sample tube was inserted into the magnet using a Sample Jet accessory. All experiments were performed at 298 K. Number of scans were 24.

Example 1

Preparation of (6R, 7R)-4-methoxybenzyl-7-((Z)-2-(5-amino-1,2,4-thiadiazol-3-yl)-2-(((1-(tert-butoxy)-2-methyl-1-oxopropan-2-yl)oxy)imino)acetamido)-3-(chloromethyl)-8-oxo-5-thia-1-azabicyclo[4.2.0]oct-2-ene-2-carboxylate (TATD-CLE)

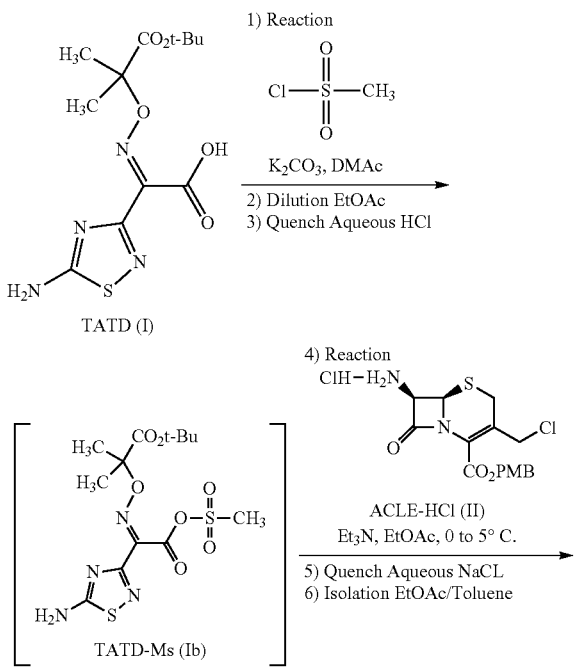

Scheme for Preparation of TATD-CLE

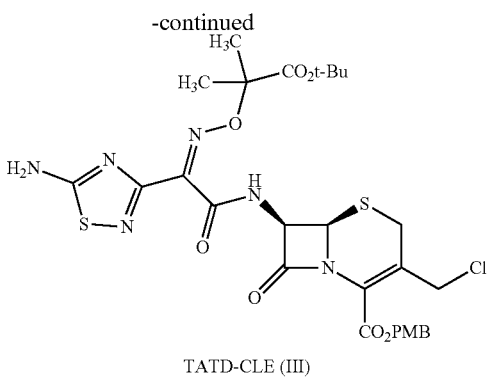

TATD-CLE (III)

Using the methods described herein, 98.7 kg of compound (I) was converted to 173.5 kg of compound (III), (TATD-CLE), an 80.1% yield. The conversion of compound (I) to compound (Ib) was performed by admixing, e.g., reacting, compound (I) with methanesulfonyl chloride and potassium carbonate. The conversion of compound (Ib) to compound (III) was performed by reaction of compound of formula (Ib) with compound (II). The details of this synthesis procedure are disclosed below.

TATD (compound (I)) (98.7 kg) was dissolved in DMAc (620 L) at 0-5° C. and then methanesulfonyl chloride (68.5 kg) was added in 10 to 15 minutes followed by potassium carbonate (41.3 kg). The reaction was stirred at 3-7° C. for 1 hour then diluted with ethyl acetate (1,100 L) and washed with 1.7% concentrated HCl solution (600 L) and then a 10% sodium chloride solution (880 L). This organic solution was added to a biphasic mixture of compound (II) (115.0 kg), water (330 L) and ethyl acetate (330 L) at 0-5° C. The pH of the reaction was continuously measured and maintained at a pH of 3.2 to 3.8 using a solution of triethylamine in ethyl acetate (1:1.9). The reaction was stirred for 30 minutes and sodium chloride (10 kg) was added and stirred for an additional 30 minutes. The lower aqueous layer was separated and discarded. The ethyl acetate solution was washed with 20% sodium chloride solution (330 L). The organic solution was separated and concentrated to 220 L, then toluene (1,145 L) and TATD-CLE seed (0.6 kg) was added. The solution was stirred for 10 hours at 22° C. then cooled to 3° C. and stirred for an additional 5 hours. The product was isolated and dried to provide 173.5 kg of TATD-CLE form 1 as a white solid.

Calculation of the yield of the product was performed as shown below (from TATD)

98.7 kg TATD/330.36 MW TATD=0.2988 moles of TATD×681.18 MW TATD-CLE=theoretical yield 203.54 kg 173.5 kg TATD-CLE/203.54 kg theoretical yield=85.2% yield (not potency corrected)

148.17 kg TATD-CLE (using potency of 85.4% TATD-CLE)/203.54 kg theoretical yield=84.7% yield (TATD-CLE potency corrected)

148.17 kg TATD-CLE/184.87 kg theoretical yield=80.1% yield (from ACLE, potency corrected for ACLE and TATD-CLE).

Figure 6:
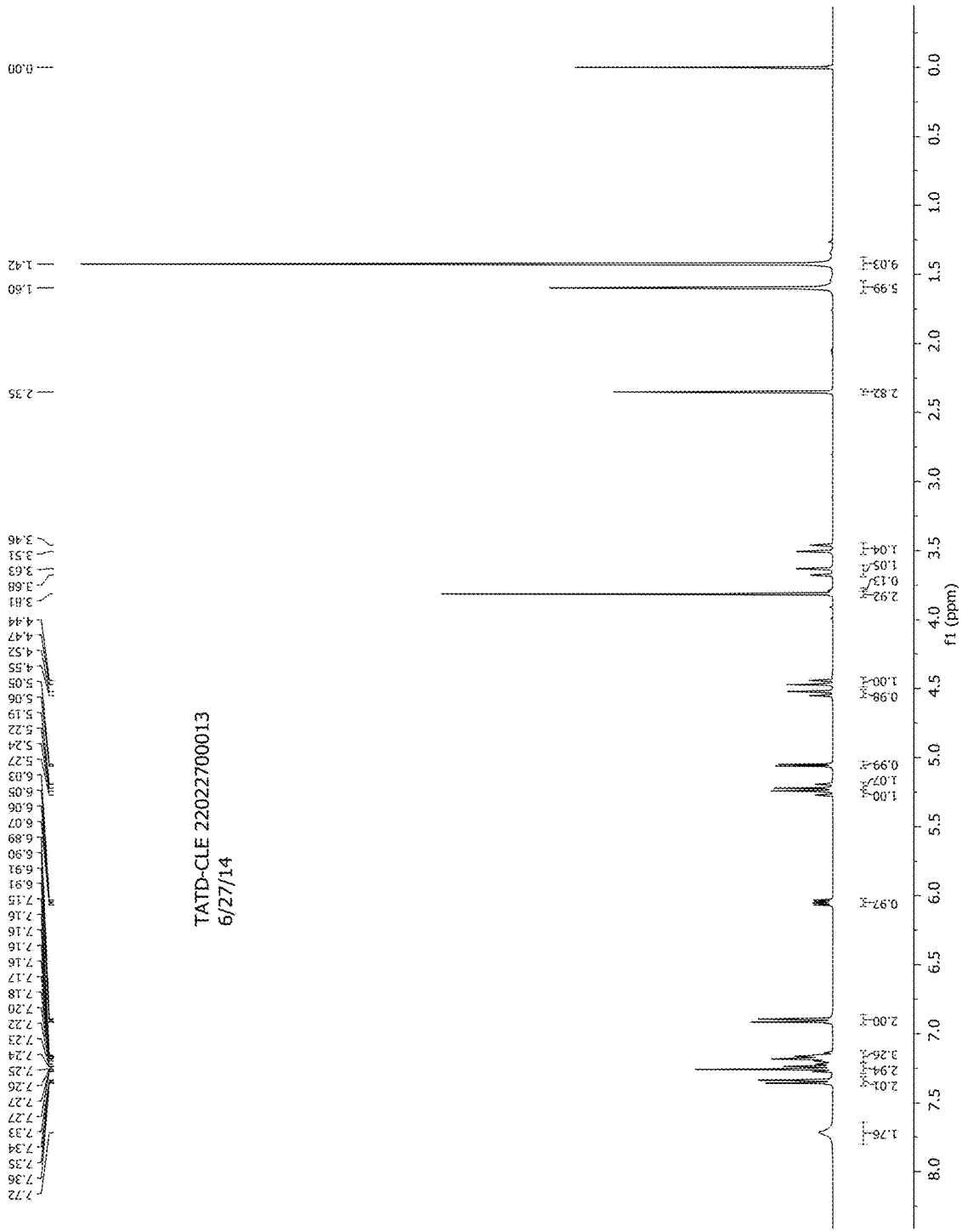
FIG. 6 shows the $^1$H-nuclear magnetic resonance (NMR) spectrum of a toluene solvate of compound (III).

Referring to FIG. 6, $^1$H-NMR spectrum of TATD-CLE toluene solvate showed signals for dimethyl protons, signals for tert-butyl protons and p-methoxybenzyl protons.

$^{1\ H\ NMR}$ (400 MHz, CDCl$_3$) δ 7.72 (s, 2H, H-17), 7.38-7.31 (m, 2H, H-11), 7.21-7.12 (m, 1H, H-14), 6.93-6.86 (m, 2H, H-12), 6.05 (dd, J=9.3, 5.0 Hz, 1H, H-7), 5.26 (d, J=11.8 Hz, 1H, H-10), 5.21 (d, J=11.8 Hz, 1H, H-10), 5.05 (d, J=5.1 Hz, 1H, H-6), 4.54 (d, J=11.9 Hz, 1H, H-9), 4.46 (d, J=11.8 Hz, 1H, H-9), 3.81 (s, 3H, H-13), 3.65 (d, J=18.3 Hz, 1H, H-2 backward), 3.48 (d, J=18.3 Hz, 1H, H-2 forward), 1.60 (s, 6H, H-15), 1.42 (s, 9H, H-16).

The NMR spectrum for TATD-CLE toluene solvate form 1 (FIG. 6) showed the presence of toluene based on the signal at 6.8-7.4 ppm for aromatic protons and signal at 2.30 ppm for methyl protons. Presence of the TATD moiety was confirmed by signals of t-butyl group and two methyl groups at 1.42 and 1.60 ppm, respectively. Presence of the p-methoxybenzyl ring was confirmed based on the signal at 6.8-7.4 ppm for aromatic protons, signal at 3.81 ppm for methoxy group and signals at 5.27-5.19 ppm for methylene group. Presence of CLE ring was confirmed based on the signal at 6.05 and 5.05 ppm for protons on the four membered ring, signal at 3.46-3.81 ppm and signal at 4.42-4.60 for methylene protons.

The level of toluene in TATD-CLE toluene solvate form 1 was determined by residual solvent content analysis by gas chromatography (FIGS. 7 and 8).

Example 2

Alternate Preparation of a Crystalline Form of Compound (III)

An alternate protocol is similar to that described in Example 1, with the following modifications that are carried out according to the process parameters in Table 3 described above.

Subsequent to the reaction to form TATD-CLE, extraction with ethyl acetate, and 20% sodium chloride solution wash as described in Example 1, the combined organic extracts are concentrated to from about 2.5 to about 3.5 volumes. Toluene (from about 0.5 to about 1.5 volumes, target value of 1 volume) and seed crystals (from about 3.0 to about 5.0 weight %, target value of 4.0 weight %) are added. The solution is stirred for from about 2 to about 4 hours, then additional toluene (from about 8 to about 10 volumes, target value of 9 volumes) is added at a rate of from about 0.4 to about 1 vol/h. The resulting solution is stirred for from about 3 to about 5 hours, then is cooled to from about 0 to about 10° C. (target value of 3° C.) for about 2 hours. The product solids are filtered, and the filtered crystals washed with toluene (from about 2 to about 10 volumes, target value of 8 volumes) to afford crystalline TATD-CLE toluene solvate form 1.

Yield from ACLE to TATD-CLE (potency corrected for ACLE and TATD-CLE) is 88-92%.

Example 3

Comparative Synthesis of Compound (III) with less than 80% Yield

U.S. Pat. No. 7,192,943, column 20, line numbers 5-35, discloses the conversion of compound (I) to compound (III) with a 75.4% yield. The detailed synthesis procedure from this second comparative example is disclosed below.

To a solution of (Z)-2-(5-amino-1,2,4-thiadiazol-3-yl)-2-(1-tert-butoxycarbonyl-1-methylethoxyimino)acetic acid compound (I) (319 g) in N,N-dimethylacetamide (1.5 L) were added potassium carbonate (113 g) and methanesulfonyl chloride (126 mL) under ice-cooling. The mixture was stirred at 10° C. for 2 hours. The reaction mixture was added to a mixture of ethyl acetate and water. The organic layer was washed with water and brine to give an activated acid solution. Next, a suspension of 4-methoxybenzyl 7β-amino-3-chloromethyl-3-cephem-4-carboxylate hydrochloride compound of formula (II) (300 g) in a mixture of water (1 L) and ethyl acetate (1 L) was adjusted to pH 6 with triethylamine under ice-cooling. To the resulting mixture was dropwise added the above obtained activated acid solution at 10° C. under stirring. Stirring was continued at 5-10° C. for 1.5 hours keeping pH of the reaction mixture at 6 with triethylamine. The organic layer was separated, washed with water and brine, and evaporated in vacuo. The concentrate was poured into diisopropyl ether (15 L), and the resulting precipitate was collected by filtration and dried to give 4-methoxybenzyl 7β-[(Z)-2-(5-amino-1,2,4-thiadiazol-3-yl)-2-(1-tert-butoxycarbonyl-1-methylethoxyimino) acetamido]-3-chloromethyl-3-cephem-4-carboxylate, compound (III), (495.7 g), 75.4% yield.

8. EQUIVALENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A process for making a compound of formula (VI):

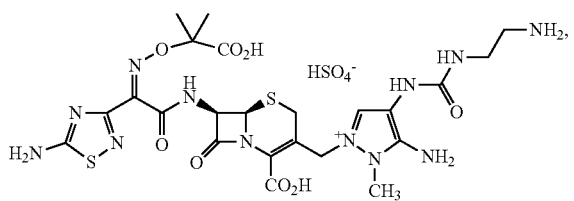

(VI)

comprising admixing a crystalline form of a compound of formula (III):

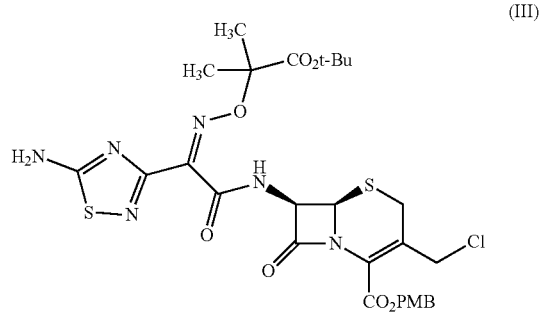

(III)

wherein PMB is 4-methoxybenzyl and wherein the crystalline form of a compound of formula (III) is a solvate of an aromatic solvent, with a compound of formula (IV):

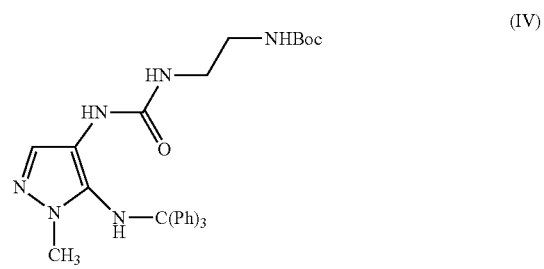

(IV)

to give a compound of formula (V):

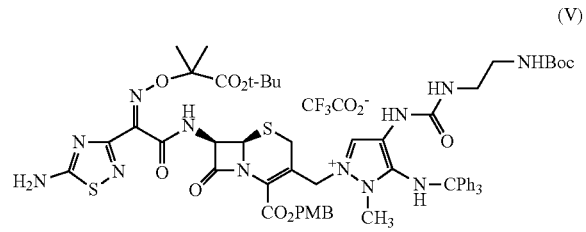

(V)

and contacting the compound of the formula (V) with a strong acid, followed by crystallization with sulfuric acid to provide the compound of formula (VI).

2. The process of claim 1, wherein the compound of formula (III), the aromatic solvent is toluene, xylene, ethylbenzene, benzene, cumene, or mixtures thereof.

3. The process of claim 2, wherein the compound of formula (III), the aromatic solvent is a toluene solvate.

4. The process of claim 1, wherein the compound of formula (III), the molar ratio of compound (III) to aromatic solvent is about 1:1.

5. The process of claim 3, wherein the crystalline form of the compound of formula (III) has an X-ray powder diffraction pattern comprising one or more characteristic peaks expressed in degrees 2θ at 6.1±0.2, 12.1±0.2, 13.1±0.2, 18.5±0.2, and 24.3±0.2.

6. The process of claim 1, wherein the strong acid is trifluoroacetic acid, sulfuric acid, formic acid, hydrochloric acid, or mixtures thereof.

7. The process of claim 1, wherein the strong acid is trifluoroacetic acid.

8. A process for making a compound of formula (VI):

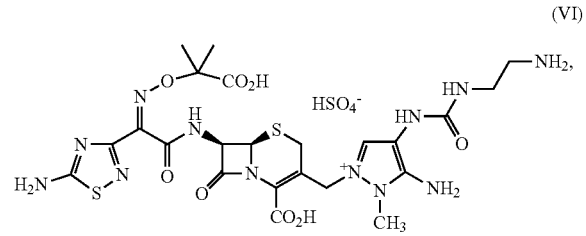 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; "HSO4-"]

(VI)

comprising admixing a crystalline form of a compound of formula (III'):

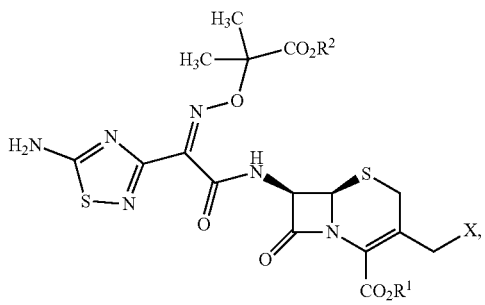

(III')

wherein
X is Cl, Br, or I; and
R¹ and R² are each independently an oxygen protecting group, and wherein the crystalline form of a compound of formula (III) is a solvate of an aromatic solvent, with a compound of formula (IV'):

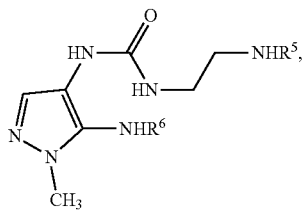

(IV')

wherein
R⁵ and R⁶ are each independently a nitrogen protecting group;

to give a compound of formula (V"):

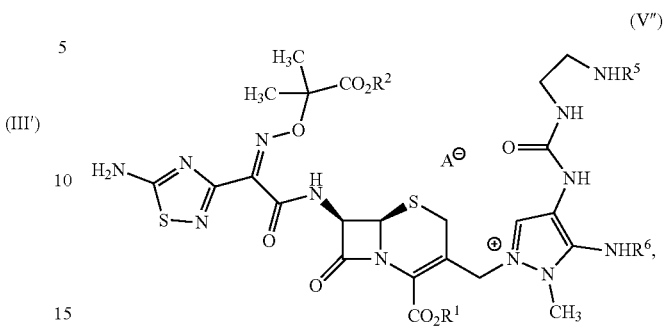

(V")

wherein $A^\ominus$ is a pharmaceutically acceptable anion;
and contacting the compound of the formula (V') with a strong acid, followed by crystallization with sulfuric acid to provide the compound of formula (VI).

9. The process of claim 8, wherein R¹ and R² are each independently tert-butyldimethylsilyl, tert-butyl, 4-methoxybenzyl, 2-methoxybenzyl, or triphenylmethyl.

10. The process of claim 8, wherein R⁵ and R⁶ are each independently tert-butyl, tert-butoxycarbonyl, 2-trimethylsilylethoxycarbonyl, or triphenylmethyl.

11. The process of claim 8, wherein the compound of formula (III), the aromatic solvent is toluene, xylene, ethylbenzene, benzene, cumene, or mixtures thereof.

12. The process of claim 11, wherein the compound of formula (III), the aromatic solvent is a toluene solvate.

13. The process of claim 8, wherein the compound of formula (III), the molar ratio of compound (III) to aromatic solvent is about 1:1.

14. The process of claim 12, wherein the crystalline form of the compound of formula (III) has an X-ray powder diffraction pattern comprising one or more characteristic peaks expressed in degrees 2θ at 6.1±0.2, 12.1±0.2, 13.1±0.2, 18.5±0.2, and 24.3±0.2.

15. The process of claim 8, wherein $A^\ominus$ is chloride, bromide, iodide, sulfate, bisulfate, tosylate, mesylate, acetate, trifluoroacetate, or triflate.

16. The process of claim 8, wherein $A^\ominus$ is sulfate.

17. The process of claim 8, wherein $A^\ominus$ is bisulfate.

18. The process of claim 8, wherein $A^\ominus$ is trifluoroacetate.

19. The process of claim 11, wherein the strong acid is trifluoroacetic acid, sulfuric acid, formic acid, hydrochloric acid, or mixtures thereof.

20. The process of claim 11, wherein the strong acid is trifluoroacetic acid.

* * * * *